United States Patent
Jayasooriya et al.

(10) Patent No.: US 9,410,888 B2
(45) Date of Patent: Aug. 9, 2016

(54) METHODS, SYSTEMS AND DEVICES FOR DETECTING INSECTS AND OTHER PESTS

(75) Inventors: Upali Abhaya Jayasooriya, Norwich (GB); Kenneth Andrew Evans, Edinburgh (GB)

(73) Assignees: University of East Anglia, Norfolk (GB); SRUC, Edinburgh (GB)

( * ) Notice: Subject to any disclaimer, the term of this patent is extended or adjusted under 35 U.S.C. 154(b) by 68 days.

(21) Appl. No.: 14/236,009

(22) PCT Filed: Jul. 12, 2012

(86) PCT No.: PCT/GB2012/051836
§ 371 (c)(1),
(2), (4) Date: Jan. 29, 2014

(87) PCT Pub. No.: WO2013/017860
PCT Pub. Date: Feb. 7, 2013

(65) Prior Publication Data
US 2014/0197335 A1    Jul. 17, 2014

(30) Foreign Application Priority Data
Jul. 29, 2011  (GB) .................................. 1113138.0

(51) Int. Cl.
*G01N 21/64* (2006.01)
*G01N 21/65* (2006.01)
*G01N 33/02* (2006.01)
(Continued)

(52) U.S. Cl.
CPC . *G01N 21/64* (2013.01); *G01J 3/44* (2013.01); *G01N 21/6486* (2013.01); *G01N 21/65* (2013.01); *G01N 33/02* (2013.01); *G01N 33/025* (2013.01); *G01N 2021/845* (2013.01); *G01N 2021/8466* (2013.01)

(58) Field of Classification Search
CPC ... G01N 21/64; G01N 21/65; G01N 21/6486; G01N 33/02
See application file for complete search history.

(56) References Cited

U.S. PATENT DOCUMENTS

| 5,118,610 | A | 6/1992 | Kitto et al. |
| 6,587,575 | B1 | 7/2003 | Windham et al. |
| 6,646,264 | B1 * | 11/2003 | Modiano et al. ......... 250/339.07 |

(Continued)

FOREIGN PATENT DOCUMENTS

| WO | WO 2007/041755 A1 | 4/2007 |
| WO | WO 2010019515 A2 * | 2/2010 |

OTHER PUBLICATIONS

International Search Report for corresponding PCT/GB2012/051836, completed Oct. 24, 2012.
(Continued)

*Primary Examiner* — David Porta
*Assistant Examiner* — Jeremy S Valentiner
(74) *Attorney, Agent, or Firm* — Tarolli, Sundheim, Covell & Tummino LLP

(57) ABSTRACT

We describe a method for detection of the presence of an invertebrate or an invertebrate component in a sample of substantially non invertebrate material, comprising impinging said sample with a source of electromagnetic radiation at a wavelength of at least 600 nm and detecting Raman scattering/fluorescence of said invertebrate or a component of said invertebrate at a wavenumber where the non-invertebrate components of said sample either do not fluoresce or fluoresce with sufficiently low intensity wherein the non invertebrate material is edible and/or living.

20 Claims, 21 Drawing Sheets

(51) Int. Cl.
  *G01J 3/44* (2006.01)
  *G01N 21/84* (2006.01)

(56) References Cited

U.S. PATENT DOCUMENTS

| | | | |
|---|---|---|---|
| 6,770,453 B1 | 8/2004 | Payne et al. | |
| 7,288,768 B2 | 10/2007 | Gore et al. | |
| 7,787,111 B2 | 8/2010 | Kim et al. | |
| 8,467,052 B1* | 6/2013 | Chao et al. | 356/301 |
| 2006/0046283 A1* | 3/2006 | Park et al. | 435/69.1 |
| 2007/0238147 A1* | 10/2007 | Okamoto et al. | 435/34 |
| 2009/0185182 A1* | 7/2009 | Kim et al. | 356/302 |
| 2009/0306521 A1* | 12/2009 | Ermakov | A61B 5/0075 600/477 |
| 2010/0185064 A1* | 7/2010 | Bandic | A61B 5/0059 600/306 |
| 2010/0248268 A1* | 9/2010 | Woods et al. | 435/7.72 |
| 2013/0296710 A1* | 11/2013 | Zuzak et al. | 600/476 |

OTHER PUBLICATIONS

Capozzi, et al.: "*Raman and Optical Spectroscopy of Eumelanin Films*", Journal of Molecular Structure, Elsevier, Amsterdam, NL, vol. 744-747, Jun. 3, 2005, pp. 717-721, XP004892272, ISSN: 0022-2860, DOI: 10.1016/J. Molstruc.2004.11.074, p. 717-718, right-hand column; figure 2.

Centeno, et al.: "*Surface Enhanced Raman Scattering (SERS) and FTIR Characterization of the Sepia Melanin Pigment Used in Works of Art*", Journal of Molecular Structure, Elsevier, Amsterdam, NL, vol. 873, No. 1-3, Jan. 11, 2008, pp. 149-159, XP022419386, ISSN: 0022-2860, DOI: 10.1016/J.,Molstruc.2007.03.026 Abstract.

Edwards, et al.: "*Raman Microspectroscopic Studies of Amber Resins with Insect Inclusions*", Spectrochimica Acta. Part A: Molecular and Biomolecular Spectroscopy, Elsevier, Amsterdam, NL, vol. 68, No. 4, Nov. 15, 2007, pp. 1089-1095, XP022346899, ISSN: 1386-1425, DOI: 10.1016/J.SAA.2006.11.037, the whole document.

Guan, et al.: "*Insect Monitoring with Fluorescence Lidar Techniques: Field Experiments*", Applied Optics, Sep. 20, 2010, vol. 49, No. 27, pp. 5133-5142.

Kalasinsky, et al.: "*Infrared and Raman Microspectroscopy of Foreign Materials in Tissue Specimens*", Spectrochimica Acta Part A 61 (2005) 1707-1713, 1701-1713 www.sciencedirect.com pp. 1701-1713.

Ozaki, et al.: "*Potential of Near-Infrared Fourier Transform Raman Spectroscopy in Food Analysis*", Applied Spectroscopy, vol. 46, No. 10, Oct. 1992, pp. 1503-1507, XP002685872, p. 1503, left-hand column-right-hand column, paragraph 2, figures.

* cited by examiner

METHODS, SYSTEMS AND DEVICES FOR DETECTING INSECTS AND OTHER PESTS

RELATED APPLICATIONS

The present invention is a U.S. National Stage under 35 USC 371 patent application, claiming priority to Serial No. PCT/GB2012/051836, filed on 27 Jul. 2012; which claims priority from GB 1113138.0, filed 29 Jul. 2011, the entirety of both of which is incorporated herein by reference.

FIELD OF THE INVENTION

This invention relates to a spectroscopic method, system and apparatus for detection of invertebrates or invertebrate components, such as insects and other pests and components thereof, in harvesting, processing and preparation stages of prepared foods and in other applications.

BACKGROUND TO THE INVENTION

The 'Prepared Salads' industry produces a 'ready to eat' product. Therefore, consumers expect these products to be safe, convenient and free from foreign bodies and/or contaminants. However, the nature of outdoor salad crop production means that there is an ever-present risk of contamination in the raw materials grown for prepared salads. This contamination can take many forms, but, notably, includes the presence of insects (pests and 'casual intruders') or other invertebrates, including organisms that alight on crop stands, for example, or which can fall into or otherwise be included in the processing chain.

At present, no comprehensive method exists to detect and remove these contaminants. The industry's current approach relies on a series of (imperfect) 'hurdles' designed to reduce the likelihood of insect contamination. These hurdles include harvester design (riddle belts, air separators etc.) and some (factory based) vision equipment. However, most operations rely primarily on manual inspection and removal. The inherent weaknesses of this approach and increasing labour costs are requiring processors to look towards other technologies.

A number of vision systems are in commercial operation. These tend to be based on visible and/or infra-red light and utilise conventional cameras together with software capable of interpreting the images received. Recent advances in (notably) software development have made a number of systems commercially viable. However, this equipment still has significant drawbacks: Differentiation between 'good' and 'bad' material is insufficient—leading to a high level of 'false positives', leading to unnecessary loss of otherwise good product, or inadequate rejection rates, resulting in contaminated product. Also, even with the most sophisticated equipment, 'shadowing' takes place where contaminants are shielded by crop material.

Metal detectors and X-ray scanners are established technologies which can effectively recognise foreign bodies on the basis of electrical properties or density. However, technologies for detecting foreign bodies, such as insects, wood, and plastics, are limited and there is significant potential for improvement. The dietary imperative to increase fruit and vegetable consumption has put new focus on the consumer acceptability of fresh fruit and vegetable produce, including elimination of insects from fruit and vegetable crops, a task made more important by the concomitant consumer pressure to reduce pesticide use. The most challenging task is perhaps the detection of insect fragments in bagged leaf salads.

Further background prior art can be found in:
"Infrared and Raman microspectroscopy of foreign materials in tissue specimens" Kalasinsky, K S; Kalasinsky, V E, Spectrochimica Acta part A—Molecular and Biomolecular Spectroscopy Vol 61 Iss 7Pps: 1707-1713, 2005
"Raman microspectroscopic studies of amber resins with insect inclusions", Edwards, H G M, Farwell, D W; Villar, S E J, Spectrochimica Acta part A—Molecular and Biomolecular Spectroscopy Vol 68 Pps: 1089-1095, 2007
"Potential of Near-Infrared Fourier Transform Raman Spectroscopy in Food Analysis" Ozaki, Y. Cho, R., Ikegaya, K., Muraishi, S., Kawauchi, K. Applied Spectroscopy, Vol 46, Iss 10, pp. 1503-1507, 1992
"Insect monitoring with fluorescence lidar techniques: field experiments", Guan et al., Applied Optics, Vol. 49, No. 27, pp. 5133-5142, in which required the capture of test species, dusting with characteristic fluorescent dye powders, and then monitoring the thus treated insects after release.
U.S. Pat. No. 6,770,453, "Methods of Detecting Chitinous Material in Non-Chitinous Biological Material".
U.S. Pat. No. 7,288,768, "Method for Measuring the Amount of an Organic Substance in a Food Product with Infrared Electromagnetic Radiation".
U.S. Pat. No. 5,118,610, "Techniques for Detecting Insect Contamination of Foodstuffs", which utilizes a biochemical assay to detect chitin.
U.S. Pat. No. 7,787,111, "Simultaneous Acquisition of Fluorescence and Reflectance Imaging Techniques with a Single Imaging Device for Multitask Inspection".
U.S. Pat. No. 6,587,575, "Method and System for Contamination Detection during Food Processing".

There remains, however, a long felt need for new sensing technologies to provide an enhanced level of detection in food handling and other environments to detect and remove insect and other contaminants.

SUMMARY OF THE INVENTION

According to the present invention there is therefore provided a method for detection of the presence of an invertebrate or an invertebrate component in a sample of substantially non invertebrate material, comprising impinging said sample with a source of electromagnetic radiation at a wavelength of at least 600 nm and detecting fluorescence of said invertebrate or a component of said invertebrate at a wavenumber where the non-invertebrate components of said sample either do not fluoresce or fluoresce with sufficiently low intensity wherein the non invertebrate material is edible and/or living.

A method, system and apparatus is described herein for non-destructively detecting contaminants in food, including but not limited to insects, for example, which might be included in prepared packages of leaf lettuce and the like.

In a related aspect the present invention provides a system for detection of the presence of an invertebrate or an invertebrate component in a sample of substantially non-invertebrate material for use in a method as described above, which comprises: a source of electromagnetic radiation for impinging electromagnetic radiation at a wavelength of at least 600 nm or 700 nm; and a fluorescence detector for detection of fluorescence of said invertebrate or an invertebrate component at a wavenumber where the non-invertebrate components of said sample either do not fluoresce or fluoresce with sufficiently low intensity.

In a further related aspect the present invention provides apparatus for use in a method as described above, which comprises: a source of electromagnetic radiation (EMR; 110)

for impinging electromagnetic radiation at a wavelength of at least 600 nm a fluorescence detector for detection of fluorescence of said invertebrate or an invertebrate component at a wavenumber where the non-invertebrate components of said sample do not fluoresce or fluoresce with sufficiently low intensity.

Embodiments of the invention provide a method, system and instrument for use in the food processing environment to detect insect or other pest contamination in non invertebrate material, for example prepared foods.

Embodiments of the invention also provide an instrument for detection of insects and other pests in prepared food items.

Embodiments of the invention also provide a method and a system to detect insects and other pests in prepared food samples.

Embodiments of the invention also provide a method and system to detect insects and other pests in food samples prior to processing.

Embodiments of the invention also provide a method, system and apparatus for improving cut flower and other horticultural products by detecting and eliminating insects or other pests that might otherwise be present.

Embodiments of the invention also provide a method for reducing pesticide use by providing a method, system and apparatus for detecting insect or other pest infestation and applying pesticides only when and where required, or to otherwise eliminate or reduce the need for pesticides by permitting manual or mechanized removal of pests identified by the system, method and apparatus of this invention.

Embodiments of the invention also provide a method, system and apparatus for use in biosecurity applications to assist in controlling the spread of undesirable pests.

Detection of Invertebrate Matter in Edible Plant Material

The investigators have determined that the pigment melanin (and chemical precursors to melanin) is apparently responsible for the observed spectral discrimination between the animal and plant species.

Thus in a further aspect the invention provides a method of detecting the presence of an invertebrate or an invertebrate component in a plant-based foodstuff, in particular as recited in any preceding claim, the method comprising using one or both of fluorescence and Raman spectroscopy to detect melanin and/or a melanin precursor in said foodstuff, wherein said fluorescence/Raman spectroscopy employs optical excitation at a wavelength longer than 600 nm, and detects fluorescence/Raman scattering from said invertebrate or invertebrate component.

In preferred embodiments the optical excitation comprises laser excitation, preferably at a wavelength longer than 700 nm to further distance the excitation from that giving rise to chlorophyll fluorescence (although seeds, for example, do not contain significant chlorophyll). In embodiments a near infrared laser is employed at a wavelength of longer than 750 nm, for example a semiconductor laser or YAG laser; optionally the laser may be tunable. In theory the shorter wavelength absorption peak of melanin should result in enhanced fluorescence/Raman scattering, but in practice the aforementioned wavelengths are preferable to reduce re-absorption of the scattered radiation. A preferred wavelength range is in the valley of the absorption spectrum of melanin in the range 1000 nm to 1900 nm. In some embodiments the method may detect fluorescence/Raman scattering at at least one wavenumber in the range 100 cm$^{-1}$ to 2800 cm$^{-1}$.

Embodiments of the method avoid absorption from the overtone bands of water by filtering out or disregarding data within a threshold range of these bands, for example avoiding by 5% on either side one or more of the following wavelengths: 1450 nm, 1190 nm, 970 nm, 836 nm, 739 nm, and 660 nm.

Some embodiments of the method detect fluorescence/Raman scattering at at least one wavenumber in the range 100 cm$^{-1}$ to 2800 cm$^{-1}$. Preferably, however, the method integrates the fluorescence/Raman scattering over a range of wavenumbers, as this helps to discriminate the melanin signal (and/or signal from chemical precursors to melanin) from other potentially interfering signals. In embodiments the wavenumber range of integration of intensity is relatively large, for example at 25% of a centre wavenumber of the range, for example a range defined by 3 dB points on a curve indicating a response of a detection system.

Surprisingly, experiments have shown that such techniques are effective at identifying the presence of invertebrate matter even when this is obscured by plant material such as a leaf and/or when the food stuff is packaged in transparent or coloured plastic packaging. In these cases it is particularly helpful to detect the Raman scattered radiation in both reflection and transmission and to employ both these in detecting invertebrate presence, for example by combining (summing) the respective signals.

Experiments have determined that amongst the materials which might be found in a plant-based foodstuff contaminated with invertebrate matter, melanin appears to be the only component which exhibits a broad fluorescence/Raman signal. Thus preferred embodiments of the method comprise distinguishing a broadband fluorescence/Raman scattering response from one or more sharper peaked/narrowband fluorescence/Raman scattering responses, to identify the presence of melanin and/or chemical precursors to melanin, and hence invertebrate contamination. In embodiments the fluorescence signal is larger and easier to detect than the Raman scattering signal, and thus in embodiments detection of a fluorescence signal may be preferred.

Some preferred embodiments of the method employ an excitation wavelength in a window which avoids absorption by both chlorophyll and water and which overlaps with the target fluorescence/Raman spectrum of melanin. For good transmittance through leaves it is advantageous to avoid the region around 700 nm (+/−50 nm at least) and the region <550 nm. Other considerations apart it might be considered that to excite fluorescence from melanin shorter wavelengths might be better (there is a small peak at 1900 nm but this can be difficult to detect because of water absorbance). More broadly, there is a balance of competing factors and, in practice, excitation in the near IR (infrared) has been found to be effective, in particular >750 nm, for example up to ~1400 nm, in embodiments in the range 750-1100 nm. This range is particularly effective at distinguishing invertebrate from plant material. Experimental detection success has been seen in this range, for example at 780 nm (+/−50 nm) and 1064 nm (+/−50 nm) with both fluorescence and Raman scattering signals.

In some embodiments fluorescence is observed at 500-5000, more particularly 1000-3000, for example 1500-2000 wavenumbers off the excitation line (to the longer wavelength side). In wavelength terms, fluorescence may be observed at >30 nm, 50 nm or 70 nm, for example ~100 nm from the excitation line. The fluorescence signal is typically several orders of magnitude lower than the laser than the laser illumination level, although perhaps two or three orders of magnitude greater than the Raman signal.

In embodiments, to detect these low level signals one or multiple interference (notch) filters are employed to separate the signal from the background. Optionally spatial filtering may also be employed, for example integrating the intensity of the return signal over a spatial region. Additionally or alternatively image processing may be employed to search for signals with the expected spatial shape of a target—which may be approximately a rectangle for an invertebrate. This may involve masking, correlation or similar spatial filtering to identify a target shape or more sophisticated processing (for example Bayesian processing), may be employed.

In a related aspect the invention provides an optical foodstuff quality control system for detecting the presence of an invertebrate or an invertebrate component in a plant-based foodstuff, the system comprising: a fluorescence/Raman spectrometer to remotely interrogate a fluorescence/Raman scattering response of said foodstuff; and a data analysis system, coupled to said fluorescence/Raman spectrometer, to analyse said fluorescence/Raman scattering response to determine the presence of said invertebrate/invertebrate component dependent on a level of melanin and/or melanin precursor indicated by said fluorescence/Raman scattering response.

In preferred embodiments the Raman spectrometer comprises an optical excitation source, in particular an infra-red laser arranged to illuminate the foodstuff, and a light collection system, which may be an imaging system, to collect the Raman scattered light from the foodstuff. This is coupled to wavelength selection optics to attenuate the laser light to facilitate distinguishing the Raman scattered light; this optics may comprise, for example, an optical notch filter and/or (holographic) grating. This in turn provides light to detector such as a CCD (charge coupled device) detector or photomultiplier.

Preferred embodiments of the data analysis system are configured to distinguish the broadband Raman scattering response of melanin from more sharply peaked responses from other materials to thereby identify invertebrate contamination. One way in which this may be performed is by integrating the Raman scattered light intensity over a relatively broad wave number range and then applying a threshold, which may be an adaptive threshold.

As previously described, in embodiments the wavelength selection optics may comprise at least one interference filter. In embodiments the detector comprises an imaging detector (camera), for example for spatial integration of the target signal.

In some preferred embodiments of the system the optical excitation source is configured to scan or illuminate a line; the system may then conveniently be orientated such that the line crosses a conveyor belt carrying the foodstuff(s) to be screened. Further, such an approach improves the signal to noise ratio of the target signal.

Other advantages of the invention disclosed herein will become apparent to those skilled in the art upon review of the entire disclosure and the appended claims.

BRIEF DESCRIPTION OF THE DRAWINGS

These and other aspects of the invention will now be further described, by way of example only, with reference to the accompanying figures.

DETAILED DESCRIPTION OF PREFERRED EMBODIMENTS

Figure 1:
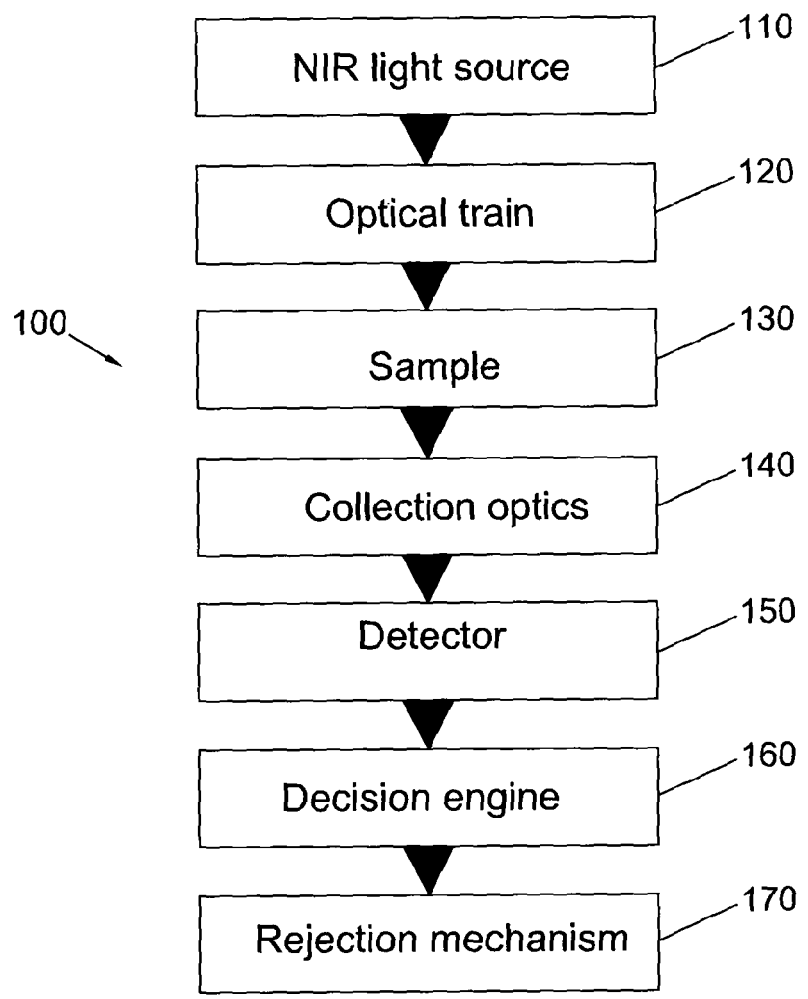
FIG. 1: A schematic representation of the elements of one embodiment of a system, method and apparatus according to this invention.

Broadly speaking we will describe modifications of techniques based on LIDAR (LIght Detection And Ranging) for detection of contaminants in salad leaves and in other food processing and other divergent application areas, to improve the quality and consumer acceptability of a wide range of products.

The innovative approach to detection of insects and other pests disclosed herein utilises a spectral characteristic of the target organisms. It results in a means of very sensitive and non-invasive detection of invertebrate organisms, even when they are hidden in a food or other matrix. It is believed that the underlying principle is generic and that therefore the detector and system disclosed herein does not need to be empirically adjusted or "trained" to recognise pests that have not been previously presented, although, of course, routine optimization (depending on the nature of the sample matrix and contaminants) is fully contemplated herein. As a result, performance of the method, device and system of this invention will outstrip current, insufficient, solutions known in the art and will provide the performance levels required by the food and other industries currently suffering losses or other pressures due to invertebrate infestations. The technique will provide both hugely increased sensitivity and a major improvement in avoiding false positives.

The innovation presented here will also be usable in a large variety of other applications where detection of insects is required in both food and non-food related areas. There will be a reduction in environmental impact: by identifying contaminants in-line before packaging, the technique will minimise the consequent waste associated with packaging and shipment of faulty goods. The technology will also reduce the risk and associated cost of recalls due to insect contamination. The system, method and apparatus disclosed herein also facilitates detection of contaminants present in product even when the product (e.g. salad leaves and the like) are already within packaging material.

Those skilled in the art will appreciate, based on the present disclosure, that various means for optimising, altering or enhancing the measurement conditions disclosed herein may be achieved, without thereby departing from the heart of the invention disclosed herein, and without incurring the need for undue experimentation.

We disclose herein a fluorescence effect in invertebrate samples when their Raman spectra are measured using exciting radiation in the near-infrared region. We show this effect is reproducibly achieved for beetles, caterpillars, moths, slugs and spiders, which are known to be the species of greatest importance to the end-users in the food-processing and other industries. While it is known that insects fluoresce using conventional excitation wavelengths, the effect disclosed herein and for which there is significant commercial potential, is the induction of insect and other invertebrate fluorescence at much longer wavelengths, which, at the same time, produces little or no fluorescence in the leafy tissues or other matrices of interest, as further discussed and disclosed herein.

Without wishing to be bound by mechanistic considerations, based on spectroscopic data provided herein, it is our hypothesis that the effect seen is due to the haemolymph (blood) or a component thereof of invertebrates, or melanin and/or chemical precursors to melanin.

Thus, in one aspect, the invention relates to a method for detection of an invertebrate or an invertebrate component in a sample of substantially non invertebrate material, comprising impinging said sample with a source of electromagnetic radiation at a wavelength of at least 600 nm and detecting fluorescence of said invertebrate or a component of said invertebrate at a wavenumber where the non-invertebrate components of said sample either do not fluoresce or fluoresce with sufficiently low intensity. The method permits clear detection of fluorescence due to said invertebrate or component of said invertebrate. In one embodiment, the material is not amber. In a preferred embodiment, the non invertebrate material is edible and/or living material. Thus, the invention relates to a method for detection of the presence of an invertebrate or an invertebrate component in a sample of substantially non invertebrate material, comprising impinging said sample with a source of electromagnetic radiation at a wavelength of at least 600 nm and detecting fluorescence of said invertebrate or a component of said invertebrate at a wavenumber where the non-invertebrate components of said sample either do not fluoresce or fluoresce with sufficiently low intensity wherein the non invertebrate material is edible and/or living.

In one embodiment, the sample is plant material.

Invertebrates of interest according to the invention include, but are not limited, to beetles, caterpillars, moths, slugs and spiders. Components of invertebrates refers, for example, to body parts thereof.

A skilled person will understand that according to the methods disclosed herein, the intensity of the laser is such that the sample is not destroyed or damaged.

In one embodiment, FT-Raman spectroscopy is carried out according to this invention using 1064 nm laser excitation. This is not the exclusive excitation wavelength at which this invention is operative, however, and those skilled in the art will appreciate that other wavelengths may be utilized. Detection has already been shown to be successful at other NIR wavelengths. Choice of wavelength to be used may depend on such factors as ease of penetration of the incident light, sensitivity of detection required, laser power and cost considerations. Those skilled in the art will appreciate that longer wavelengths will provide better penetration while shorter wavelengths will provide better sensitivity. The selected wavelength will determine the cost of the laser and also the detector.

Figure 10:
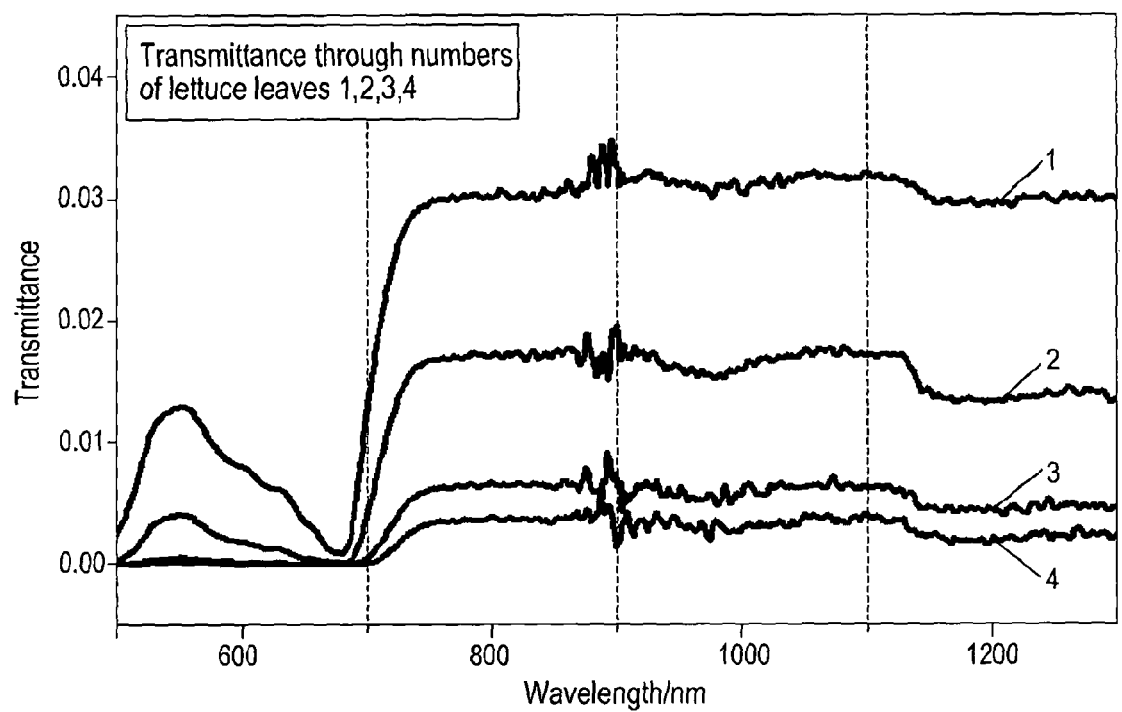
FIG. 10: How the transmittance of salad leaves depends on their numbers, measured across the visible to near infrared region, showing the maximum transmittance window from about 750 nm to longer wavelengths, including but no limited to 1064 nm.

As shown in FIG. 10, the whole of the wavelength region longer than about 750 nm provides a large window with salad materials for deep spectroscopic probing with techniques such as Raman and Fluorescence spectroscopies.

At least two major advantages are offered by using wavelengths in the NIR range. The most significant is that relatively few compounds fluoresce at such long wavelengths, leading to the discrimination of the presence of pests, which, as we show herein, contain components which do fluoresce at these long wavelengths. The second is that light at NIR wavelengths has the ability to penetrate plant material, enabling detection of pests and pest components within or behind the plant material. Longer wavelengths in general give better penetration of the sample, but since the strength of the Raman effect, on which the detection depends, exhibits a dependency on the fourth power of the wavelength, shorter wavelengths within the ranges disclosed herein, can be expected to give higher sensitivity.

FT-Raman spectroscopy may be carried out according to this invention using single or multiple wavelengths, for example, using both 750 nm and 1064 nm laser excitation, as well as excitation at any wavelength between these extremes. It is also possible to produce spectra by moving through different excitation wavelengths in a given range of wavelengths and to collect fluoresce spectra, Raman spectra or both fluoresce spectra and Raman spectra from samples thus illuminated. These are not the exclusive excitation wavelengths at which the invention is operative, and those skilled in the art are able, based on this disclosure, to arrive at optimized excitations for particular samples and contaminants, to thereby minimize background noise and enhance the signal to noise ratio. Thus, according to the invention, excitation is at about 600 nm to about 1300 nm, for example at about 750 nm to about 1064 nm. In one embodiment, excitation may be at 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm, 1000 nm, 1005 nm, 1010 nm, 1015 nm, 1020 nm, 1025 nm, 1030 nm, 1035 nm, 1040 nm, 1045 nm, 1050 nm, 1055 nm, 1060 nm, 1065 nm, 1070 nm, 1075 nm, 1080 nm, 1085 nm, 1090 nm, 1095 nm, 1100 nm, 1110 nm, 1120 nm, 1130 nm, 1140 nm, 1150 nm, 1160 nm, 1170 nm, 1180 nm, 1190 nm, 1200 nm, 1210 nm, 1220 nm, 1230 nm, 1240 nm, 1250 nm, 1260 nm, 1270 nm, 1280 nm, 1290 nm or 1300 nm or a combination thereof to give multiple spectra, and intermediate wavelengths are all contemplated herein. It is noted that the red edge of the chlorophyll spectrum (about 760 nm) out to a longer wavelength than 1064 nm approaches the lower working end for the method of the current invention for chlorophyll containing materials. However, the issue with chlorophyll is not a sharp transition, such that working information is obtainable even down to about 700 nm. The absorption by chlorophyll plateaus at approximately 750 nm and therefore can easily be corrected for and addressed in the present invention at or above that wavelength. It should further be noted that non-chlorophyll containing food products will not suffer from this absorption effect to same degree and thus lower wavelengths may be utilizable than where chlorophyll-containing materials are included in the samples. In addition, it will be appreciated that by merely utilizing the elements of the present invention at a wavelength of, say, 600 nm, or 1080 nm, would be equivalent to utilizing the elements of the present invention at a wavelength as defined, herein above, between about 750 nm and 1064 nm, and should not be considered to be outside the scope of the present invention. In a preferred embodiment according to this invention, excitation is at a wavelength between about 750 nm and 1064 nm, including the end limits on either side (i.e. 750 nm and 1064 nm) of the range. Of course, those skilled in the art will appreciate that running spectra across a range of wavelengths may well provide an optimal wavelength for carrying out the process of the present invention, without the need to test individual wavelengths, for particular samples and contaminants in those samples.

The measurements disclosed herein are accompanied by measurements of absorption spectra of each constituent, to establish the near-IR absorption features that are responsible for the observed fluorescence. Use of a tuneable light source across the NIR is ideally utilized to determine the fluorescence yields, since commercially available spectrometers do not generally permit excitation at wavelengths beyond 1010 nm. Use of a tuneable light source facilitates rapid determination of whether the excitation line used is the most appropriate for a given application. Although wavelengths other than those disclosed herein may give a better sensitivity, there will also be a trade-off against such factors as sample penetration depth, internal scattering and cost, since the more commonly used lasers are much less expensive to obtain.

The techniques described herein use a novel spectroscopic effect which offers considerably enhanced sensitivity to the presence of insect and pest species and components thereof, as compared to any method currently available, and will be effective even when the contaminant is obscured by the sample and would be undetectable by visual inspection by an operator or camera-based system. This represents a major step forward in detection of insect or other invertebrate contamination compared to anything currently available.

Although, as mentioned above, metal detectors and X-ray scanners are established technologies which can effectively recognise foreign bodies on the basis of electrical properties or density, technologies for detecting foreign bodies such as insects, wood and plastics are limited and there is significant potential for improvement. The dietary imperative to increase fruit and vegetable consumption has put new focus on the consumer acceptability of fresh fruit and vegetable produce, including elimination of insects from fruit and vegetable crops, a task made more important by the concomitant consumer pressure to reduce pesticide use. The most challenging task, as previously mentioned, is perhaps the detection of insect fragments in bagged leaf salads, and this application has, therefore, been used as a challenging focus for the system, method and apparatus disclosed herein. As discussed below, the testing we have conducted reveals that this invention provides a solution to the long-felt needs unmet by current technologies, and given its success in the very difficult test situation of detection of insect contamination in leafy material, as exemplified herein, it is anticipated that this methodology is easily extendable into a wide range of less challenging scenarios.

The present invention disclosure provides a method for spectroscopic detection of insects which allows detection of the presence of whole or parts of a variety of invertebrate species. We have discovered that invertebrates of interest, such as beetles, caterpillars, moths, slugs and spiders, show a fluorescence effect when irradiated with near-infrared light at, but not limited to, 785 nm and 1064 nm. As shown in FIG. 10, the whole of the wavenumber region longer than about 750 nm provides a large window with salad materials for deep spectroscopic probing with techniques such as Raman and Fluorescence spectroscopies.

The advantages of using light at these particular wavelengths (for example 750 nm-1064 nm) for practicing the present invention include, but are not limited to that:
  Very few compounds fluoresce at such a long wavelengths, making the detection of insects and insect components, as a result of the fluorescence reported herein, very effective
  Light in the near-infrared is capable of penetrating plant and packaging material, allowing detection of pests and intruders even if they are obscured from direct view.

Use of the fluorescence effect disclosed herein offers a considerable improvement over the current capabilities for detection of invertebrate contamination of prepared salads and other foods, and in a variety of other contexts described herein. The effect disclosed herein also offers the possibility of detection of insect and other pests in a variety of applications both food and non-food related, including but not limited to:
  Contamination of other prepared foods (meat, fruit, vegetables, salads, ready meals, baby food)
  Contamination of raw materials (meat, grain, flour, fruit, vegetables, herbs, spices)
  Detection of infestation of crops including scanning of growing plants in glasshouses and in fields
  Biosecurity applications in scanning plant material during import and export
  Examination of plants and cut flowers for infestation in horticultural applications Detection of other insect infestations such as termites and deathwatch beetle The present disclosure focuses on the application of this invention to the prepared salad application and market, because this is a particularly challenging context in which to demonstrate the operability of this invention. However, the potential applications of this technology are applicable to a wide variety of contexts and are not limited to the specific food-handling applications on which the exemplary support provided herein primarily focuses.

The technology disclosed herein is, in a first embodiment, aimed at the pre-prepared salad market. In the UK alone, 2.5 billion salad packs have been sold in the last 10 years. The UK market is estimated (Bakkavor) at >£400 million and growing. (TNS estimates potential growth at 7% per year). In Europe, the degree to which regions have embraced prepared salad varies, but a number of states have substantial markets: Italy 638M euros, France 435M euros, Spain 160M euros, Germany 160M euros, Holland 152M euros. The US market is currently $2.5 billion per annum. Market growth is stimulated by increasing awareness of the need for a variety of fresh fruit and vegetables for a healthy diet and a well-off but time-poor customer base.

Within the UK there are several producers of bagged salads, at a European level, three suppliers have substantial market shares within a more fragmented and diverse supply market. The UK market is served by around 50 processing lines, and the European market by at least 250 and with an attractive projected instrument cost of around £50 k, the development could be rapidly adopted by industry.

Prepared Salads are both minimally processed and sold as 'ready-to-eat'. Consumers expect the products they buy to be free from defects (including insect contamination), and yet manufacturers use relatively little process technology to help them achieve this.

Figure 15:
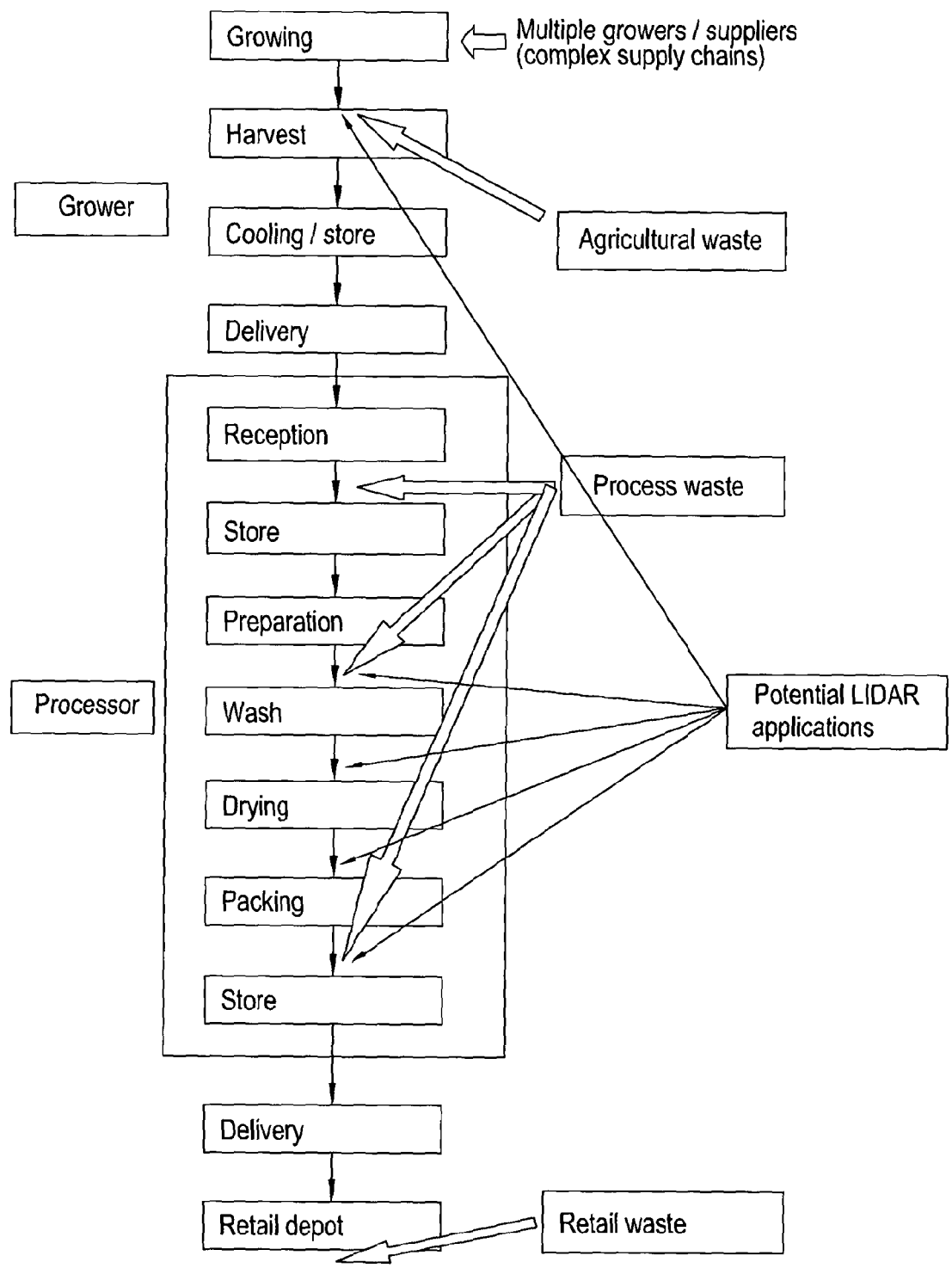
FIG. 15: Schematic of agricultural product (e.g. packaged lettuce) processing with potential points for use of the system, apparatus and method of this invention to achieve cost savings by detection and elimination of invertebrate and other pest contamination.

FIG. 15 provides one representation of the prepared salads supply chain, the typical locations where agricultural waste occurs, where processing waste occurs, and where retail waste occurs—and the points in the process where the system, method and apparatus of this invention might best be situated to eliminate or reduce each of these types of waste.

Insect contamination of salad bags is a recognised and persistent problem—and whilst insect complaint levels are said to run at around 2 per 100,000 units sold, the inefficiency of reporting systems means that actual non-conformances will be much higher. In order to maintain even this level of performance, manufacturers have to be very selective in their use of raw materials: Leaf crops showing any evidence of contamination are not permitted to enter the factory—however small that contamination level may be. As a result, contaminated crop is routinely wasted in the field—and ploughed in. Contaminated deliveries initially accepted at the factory create process waste (including energy, water and materials) and may then be rejected. Consumers are disappointed by insect contamination—leading to non-repeat purchase and lost sales/sales growth. Retailers penalise suppliers for insect complaints.

The 'upstream' supply chain for prepared salads manufacture suffers from very high levels of waste. Whilst there are many reasons for this (including weather patterns and the nature of consumer demand), the high quality standards required by manufacturers dictates that a significant proportion of the materials grown are abandoned for, essentially, cosmetic reasons. Insect contamination is a major contributor to this waste.

Crops suffering from low levels of insect contamination are frequently abandoned because the factory process for which they are destined does not have an effective way of removing these contaminants. Slugs are an excellent example of this: If a crop is seen in the field to have slug contamination it is deemed unfit to process because slugs are notoriously difficult to remove in factory wash systems. However, the absolute level of slug contamination in material harvested may be very low—perhaps as low as one or two slugs per tonne of raw material.

If effective methods of detection and removal existed, this crop could be processed and only the contaminated leaves (a few grammes of material) removed—instead of the whole field batch. This would result in a corresponding increase in agricultural efficiency. (The crop required by factories could be grown on fewer hectares—with a corresponding reduction in both inputs and carbon footprint—or, alternatively, existing hectares would become more efficient).

The quantity of crop ploughed-in as a result of contamination varies enormously. Bakkavor's main suppliers indicate that losses could be as high as 1%. If this is taken as being representative of the industry, it would suggest field losses and, therefore, waste of around £800 k (1.1 million kilos) annually.

In addition to the field waste, during processing, manufacturers will throw away crop that is delivered and accepted but later found to be contaminated. The cost of this waste is relatively low compared to the waste incurred 'in field'. Currently, no truly effective method of insect detection exists. However, records suggest that industry might discard 0.25% of raw materials 'in process' as a result of insects. Again, this is 'gross' waste and relates to material identified as being contaminated (after delivery) and, therefore, unfit for process. This is equivalent to an annual food waste of around £300 k (300 k kilos) across the industry. This, combined with the crop waste in-field, equates to a total waste of 'good' salad raw material—as a result of insect contamination—at approximately £1.1 m per year.

Customer complaints regarding insect contamination run at around 2 per 100,000 units sold. However, because reporting systems are inefficient, actual non-conformances are felt to be considerably higher. With market penetration now high in the UK (c. 75%), further growth will come from encouraging people to eat more bagged salad or buy more frequently. Current levels of insect contamination are seen as a major block to market growth. An estimated 1% of potential sales growth is lost through consumers having problems such as insect contamination of these products (equivalent to a retail value of £4 m).

Contamination issues affect the reputation and customer perception of the supplier. This is particularly influential on small-scale and artisan producers who have significant sales directly to the consumer. Organic producers have a substantial problem with insect contamination since use of conventional pesticides is not acceptable. This means that crops are prone to infestation and those following organic production protocols cannot plan any form of pesticide protection of their product. Different crops have different values, but on average organic growers would be estimated to get a return of £4000-£5000 per acre. In some seasons typical artisan producers can lose up to 15% of their production, including whole crops in the past, because they were unable to efficiently separate spoiled crop. Whilst the insect detection system proposed is targeted at the prepared salads industry, it's clear that, with little development (and at the reasonable projected cost) it would have applications for these producers. Crop can often be abandoned because of the uneconomic cost of sorting.

There are an estimated 600 registered organic fruit and vegetable producers in the UK alone1 indicating a considerable potential waste saving.

Much higher levels of contamination (and, therefore, waste) are consistently seen in organic crops. Whilst the market share of 'Organics' is small at present, it is growing—which will impact on insect based rejection and waste. In fact, the level of waste involved in organic production is one of the issues restricting growth in the category—and an effective technology for eliminating insects could have a major impact on the viability of organic prepared salads for companies such as Bakkavor.

Improving viability should stimulate and encourage the market share of sustainable production systems.

Even where pesticide use is acceptable, pesticide approvals in Europe are undergoing a substantial review. The effect of this is a significantly reduced pesticide 'armoury' for growers. Pesticide manufacturers are not spending the money necessary to research and approve pesticides for 'minor' crops and approvals are, effectively, being revoked. This means that insect contamination (and hence crop waste) may become a much greater issue for growers and processors in the next couple of years.

In addition, it is worth noting that many of the insects causing problems in salads are not pests of the crop—but are what is known as 'casual intruders'. These are non-pest species that happen to land on field crops—but do not necessarily feed there. Because of this, it is often not necessary to treat/spray crops simply to reduce contamination. If an effective system for contaminant removal was available, it may well be possible to reduce the amount of pesticide used.

There are a number of points in the supply chain where LIDAR technology (and this reference to LIDAR should be understood to be a reference to a very generic description of a technology that typically is utilized to build profiles of characteristics being measured in time-space), as modified and disclosed herein, could be used to detect and remove insect contaminants. (See FIG. 15). However, the main benefit of an effective insect identification technique (in this context) is to make otherwise unacceptable field crops processable. Therefore, the presence of the detection equipment is more important than the location of it within the supply chain. This disclosure concentrates on a device to detect contamination at the point of packaging for prepared salads. This is, however, only one among a vast variety of other applications and positions in the supply chain where the invention can exert significant cost and material savings.

Alternative applications and locations for measurement using the method, system and apparatus according to this invention may be deployed elsewhere in the processing chain, including, for example, for heterogeneous applications such as scanning incoming whole produce. One way in which this may be achieved can be appreciated by those skilled in the art, based on the present disclosure, when it is noted that long-wavelength Raman has become rugged. See, for example, Bergles et al, 2009, "Long-wavelength Raman becomes rugged", reported at http://www.optoiq.com/index/photonics-technologies-applications/lfw-display/lfw-article-display/350050/articles/biooptics-world/volume-2/issue-1/features/spectroscopy/long-wavelength-raman-becomes-rugged.html. See, also, Analytical Applications of Raman Spectroscopy, Michael J Pelletier, ISBN: 978-0-632-05305-6, March 1999, Wiley-Blackwell, herein incorporated by reference.

In this manner, additional savings could be made by avoiding the resource and energy costs associated with processing before elimination—including a reduction in wash water and chlorine effluent. However, because the absolute quantity of affected raw material rejected (and hence process input wasted) will be low, these savings are insignificant when compared to the potential reduction in agricultural waste due to abandoned crop. Ultimately the capability of LIDAR, as modified according to the present disclosure, provides a time-resolved measurement and hence spatially resolved map of the presence of a contamination, which means that it is also possible according to this invention to detect contamination of the crop whilst still in the ground, thereby allowing for remedial action in advance of harvest.

The apparatus, method and system according to this invention when applied to the bagged salad industry demonstrates the utility of this invention to, for example, prepared vegetable and fruit, whole fruit and vegetables, grain and cereal applications, ornamental, biosecurity and in-field applications. In addition to being applicable, for example, to detecting grain infestation by boring insects, there are many other application areas, such as in whole fruit, potatoes, biosecurity, ornamentals, baby food, breakfast cereals, seeds and lentils. Spatial mapping of insect infestation in growing crops and non-food applications such as infestation of wood by termites and beetles is also within the scope of applications to which the present invention may be applied.

With reference now to FIG. 1, there is provided a schematic representation of the elements of one embodiment of a system, method and apparatus according to this invention. The system/apparatus/method 100 (referred to generally herein as "the system") comprises a source of electromagnetic radiation (EMR) 110, which in the embodiment shown in FIG. 1 is a Near Infrared (NIR) source, for emitting EMR at, for example, 1064 nm (see the various wavelengths mentioned above, any of which may be appropriate for a given material and contaminant). Of course, those skilled in the art will appreciate that another, and indeed multiple other, wavelengths may be utilized for this purpose, without departing from the essence of the invention disclosed herein, provided that the wavelength(s) chosen are such that any invertebrate or invertebrate component in a sample to be analyzed fluoresces as a result of exposure to the impinging EMR wavelength, and provides an adequate signal to noise ratio (SNR) over any ambient fluorescence or fluorescence of the sample other than the invertebrate material, to reliably permit detection of the contaminants. The source of EMR may be a laser, a tungsten light or any other EMR source known in the art or which is hereafter developed. In many applications according to this invention, it is desirable for the EMR to be substantially constituted of a single wavelength, i.e. monochromatic light, of a chosen wavelength, including but not limited to 1064 nm.

The EMR 110 is focused on a sample 130 by means of an optical train 120 which may include electronic and/or glass and/or other types of lenses for focusing the EMR onto said sample 130. The optical train may likewise include apertures, filters, collimators and the like known in the art to achieve the objective of specifically illuminating the sample of interest with the portion of EMR of interest. Furthermore, the optical train 120 and point of illumination of the sample 130 in one embodiment comprises a closed housing through which the sample 130 passes, with the closed housing being provided to eliminate or reduce any stray light which may cause false signal acquisition or which might otherwise reduce the signal to noise ratio.

The sample 130 may be any material of interest, including, but not limited to, foodstuff, flowers, grain and the like, as discussed elsewhere herein, for which it is desired to determine whether invertebrate contamination is present. The sample 130 may be passed in front of the optical train 120 by way of a conveyor belt on which the sample 130 rests, or the sample 130 may be manually or mechanically passed before the optical train 120 by other means known in the art. Of course, in an embodiment according to this invention where LIDAR is being utilized to scan a field or a portion of a field or plot of land or the like, then the optical train would be directed toward such sample 130. In one preferred embodiment according to this invention, for example, the sample 130 comprises salad leaves or other edible foodstuffs, for which it is desired to confirm that there is no or a defined acceptable amount of insect, arthropod or other pest contamination.

For the detection of emitted fluorescence, there is provided collection optics 140 and at least one detector or detection system 150. Those skilled in the art will appreciate that, in general, this is known technology, for example a CCD camera. In a particular embodiment according to this invention, however, there are particular enhancements for collection of reflected light, refracted light, transmitted light as well as detection of Stokes Raman and anti-Stokes Raman light emission by the collection optics 140 and the at least one detector 150.

The detector 150 is operatively connected to a decision engine 160 which comprises appropriate algorithms, computer hardware and software, to filter the signals produced by the detector, and to discriminate signal from noise. Depending on the nature of signals obtained from the sample, the decision engine 160 provides an indicator that undesirable invertebrate contamination in the sample 130 has been detected. When this occurs, a rejection mechanism 170 desirably segregates contaminated material from non-contaminated material. This component of the system may include, but is not limited to, a chute, into which contaminated material is dropped, a diverting stream for diversion of the contaminated material to a path which avoids inclusion of the contaminated material from desired, uncontaminated material, and/or a human or robotic mechanism for specifically lifting contaminated material and removing it from the remainder of the product stream. Subsystems for this purpose are disclosed, for example, in U.S. Pat. No. 6,587,575 and U.S. Pat. No. 7,787,111, herein incorporated by reference for this purpose.

In light of the above, those skilled in the art will appreciate that this invention comprises and contemplates a method for detection of the presence of an invertebrate or an invertebrate component in a sample comprising impinging said sample with a source of electromagnetic radiation at a wavelength and a non-destructive intensity at which said invertebrate or a component of said invertebrate fluoresces and detecting said fluorescence at a wavenumber where the non-invertebrate components of said sample either do not fluoresce or fluoresce with sufficiently low intensity to permit clear detection of fluorescence due to said invertebrate or component of said invertebrate. The method preferably comprises Fluorescence spectroscopy, Raman spectroscopy, or both. Preferably, the method comprises making a comparison between Raman and Fluorescence spectroscopies to detect said invertebrate or invertebrate component in said sample. The Raman spectra comprise signals from non-invertebrate components in said sample and signals from said invertebrate or said invertebrate component in said sample, whereas said fluorescence signal is provided only by said invertebrate or invertebrate component in said sample, wherein said latter signal is greater than the former, for example several orders of magnitude greater, such as 1, 2, 3, 4, 5, 6, 7, 8, 9 or 10 times greater. This facilitates the detection of said fluorescence signals from said invertebrate or invertebrate component in said sample. The method desirably utilizes a source emitting electromagnetic radiation having a wavelength of at least about 700 nm and preferably at a wavelength of about 700 nm to 1300 nm. The light source, according to various embodiments of this invention, optionally emits electromagnetic radiation having a wavelength selected from the group consisting of 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm, 1000 nm, 1005 nm, 1010 nm, 1015 nm, 1020 nm, 1025 nm, 1030 nm, 1035 nm, 1040 nm, 1045 nm, 1050 nm, 1055 nm, 1060 nm, 1065 nm, 1070 nm, 1075 nm, 1080 nm, 1085 nm, 1090 nm, 1095 nm, 1100 nm, 1110 nm, 1120 nm, 1130 nm, 1140 nm, 1150 nm, 1160 nm, 1170 nm, 1180 nm, 1190 nm, 1200 nm, 1210 nm, 1220 nm, 1230 nm, 1240 nm, 1250 nm, 1260 nm, 1270 nm, 1280 nm, 1290 nm, and 1300 nm, or an intermediate wavelength. In a preferred embodiment according to the invention, the excitation wavelength is selected from a wavelength between about 750 nm and 1064 nm. In specific embodiments according to the invention, the light source is selected from the group consisting of a laser, a tungsten lamp, and a Xenon discharge lamp. The method of this invention may be utilized where the invertebrate is one haemolymph, melanin, or both. The invertebrate may be one selected from the group consisting of insects, arthropods, arachnids, and molluscs. Specifically, the invertebrate may be selected from the group consisting of beetles, caterpillars, moths, slugs and spiders. The method may be utilized in an industry selected from the group consisting of agriculture, food production, horticulture, biosecurity, and combating bioterrorism. The method may be used in the detection of contamination of prepared foods, raw materials, infestation of crops including scanning of growing plants in glasshouses and in fields, biosecurity threats including scanning of plant material during import and export, examination of plants and cut flowers for infestation in horticultural applications, and insect infestations including termites and deathwatch beetle. Furthermore, the method may be implemented for use in reducing or targeting the use of pesticides.

The invention may likewise be viewed as a system for detection of the presence of an invertebrate or an invertebrate component in a sample of substantially plant material which comprises: a source of electromagnetic radiation for impinging electromagnetic radiation at a wavelength of at least 700 nm; and a fluorescence detector for detection of fluorescence at a wavenumber where the non-invertebrate components of said sample either do not fluoresce or fluoresce only weakly.

The system may utilize both Raman and fluorescence spectra.

The invention may yet further be viewed as an apparatus for detection of the presence of an invertebrate or an invertebrate component in a sample of substantially plant which comprises: a source of electromagnetic radiation for impinging electromagnetic radiation at a wavelength of at least 700 nm; and a fluorescence detector for detection of fluorescence at a wavenumber where the non-invertebrate components of said sample do not fluoresce or fluoresce only weakly.

The apparatus may further comprise, with reference to FIG. 1: a source of electromagnetic radiation (EMR) 110; an optical train 120 for focusing the EMR onto a sample 130;

collection optics 140; at least one detector or detection system 150; and a decision engine 160 which comprises appropriate algorithms, computer hardware and/or software, to filter the signals produced by the detector, and to discriminate signal from noise.

The apparatus may further, depending on the nature of signals obtained from the sample, include a decision engine 160 which provides an indicator that undesirable invertebrate contamination in the sample 130 has been detected. Desirably, the apparatus, when contamination is detected, includes a rejection mechanism 170 results in the segregation of contaminated material from non-contaminated material.

In another aspect, the invention relates to the use of a method described herein in the detection of contaminated food stuff.

Those skilled in the art will appreciate that a wide variation in the particular configurations for the method, system and apparatus of this invention may be implemented, including equivalents of the various elements of the system described herein above, without departing from the essence of the invention as herein disclosed and claimed.

The methods described herein can also be used to detect melanin in a sample and to distinguish melanin-containing material from non-melanin-containing material.

In one embodiment, the methods of the invention specifically do not include imaging archaeological artefacts, for example fossilised resin such as amber.

EXAMPLES

Having generally described this invention herein above, those skilled in the art are enabled to practice this invention to the full scope as claimed herein. To further ensure that an adequate written description of this invention is provided, and that it includes a description of the best mode for practicing the invention, the further detailed examples provided herein below are provided by way of example only and are non-limiting.

Example 1

Evaluation of the Fluorescence Effect

Figure 2:
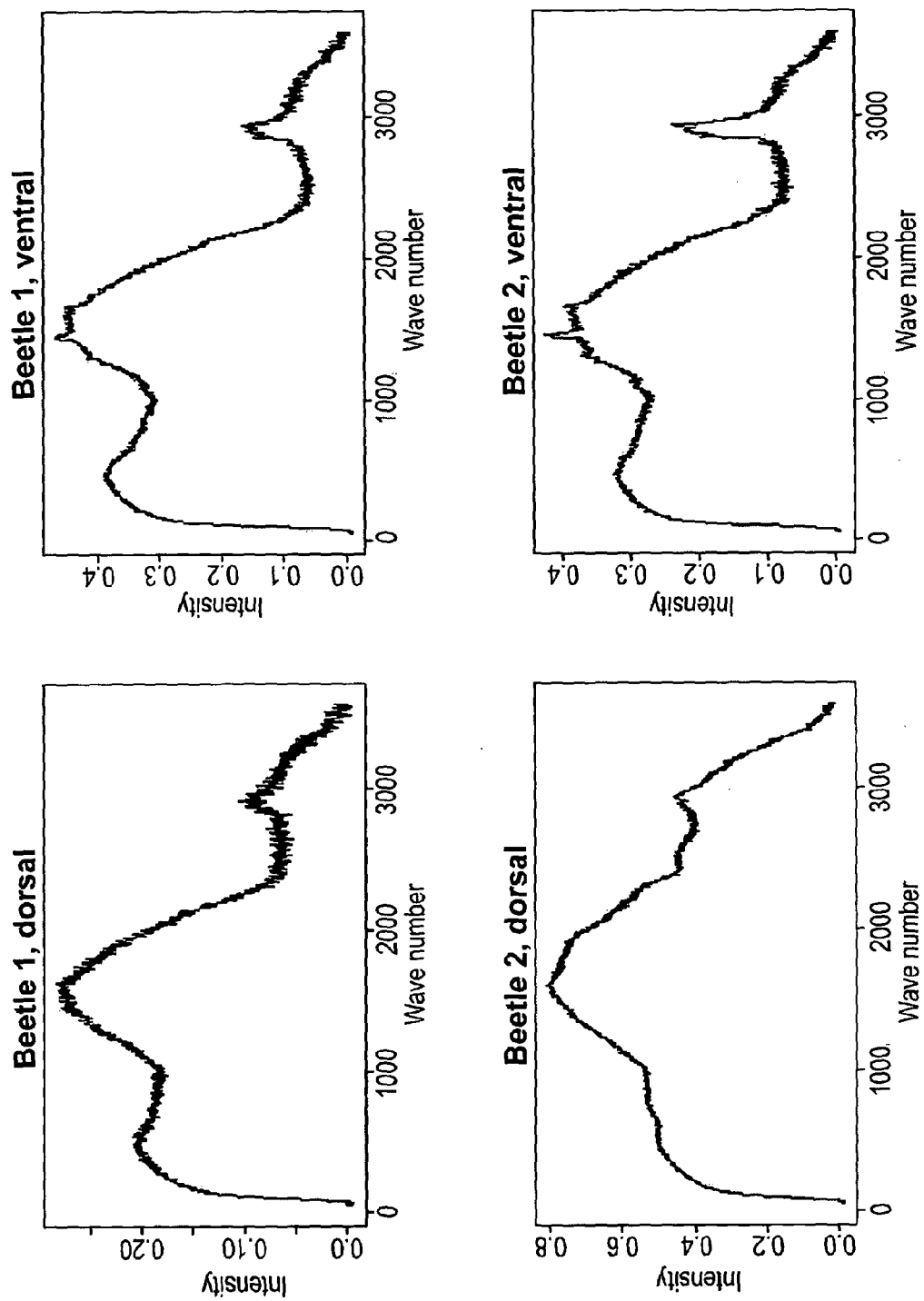
FIG. 2: Typical FT-Raman spectra with 1064 nm excitation showing broad fluorescence induced when invertebrate contamination is present.

The LIDAR technique (read broadly, as mentioned above, as the LIDAR ranging component is not tested in the results presented herein, although LIDAR may be applied in select embodiments to position detect contaminants), was expected to give high sensitivity to the presence of insects, and by selection of an appropriate laser excitation line, the contamination would not be obscured by the sample or by the packaging. In order to confirm the viability of the technique without the need to build a potentially expensive prototype, a series of conventional Raman spectra were obtained as follows:

Spectra were measured of a selection of pest species identified as being of particular importance to the food industry: beetles, caterpillars, moths, slugs and spiders using two samples of each type of pest and two orientations. For example the wings of the moths were sampled as well as the body to gauge the degree to which spectral response varied since in particular for larger insects the contaminant may not be a complete individual. FIG. 2 shows examples of typical Raman spectra, obtained with 1064 nm excitation, showing broad fluorescence features. Analysis of the results showed that all the insect samples showed significant fluorescence resulting in a much stronger Raman response than would be expected under normal measurement conditions, see FIGS. 2, 4, 5, 6, and 7. The fluorescence covers a wide frequency range, making selection of a measurement range straightforward. The fluorescence seen was confirmed on a second spectrometer, and was, therefore, not a measurement artefact.

Figure 11:
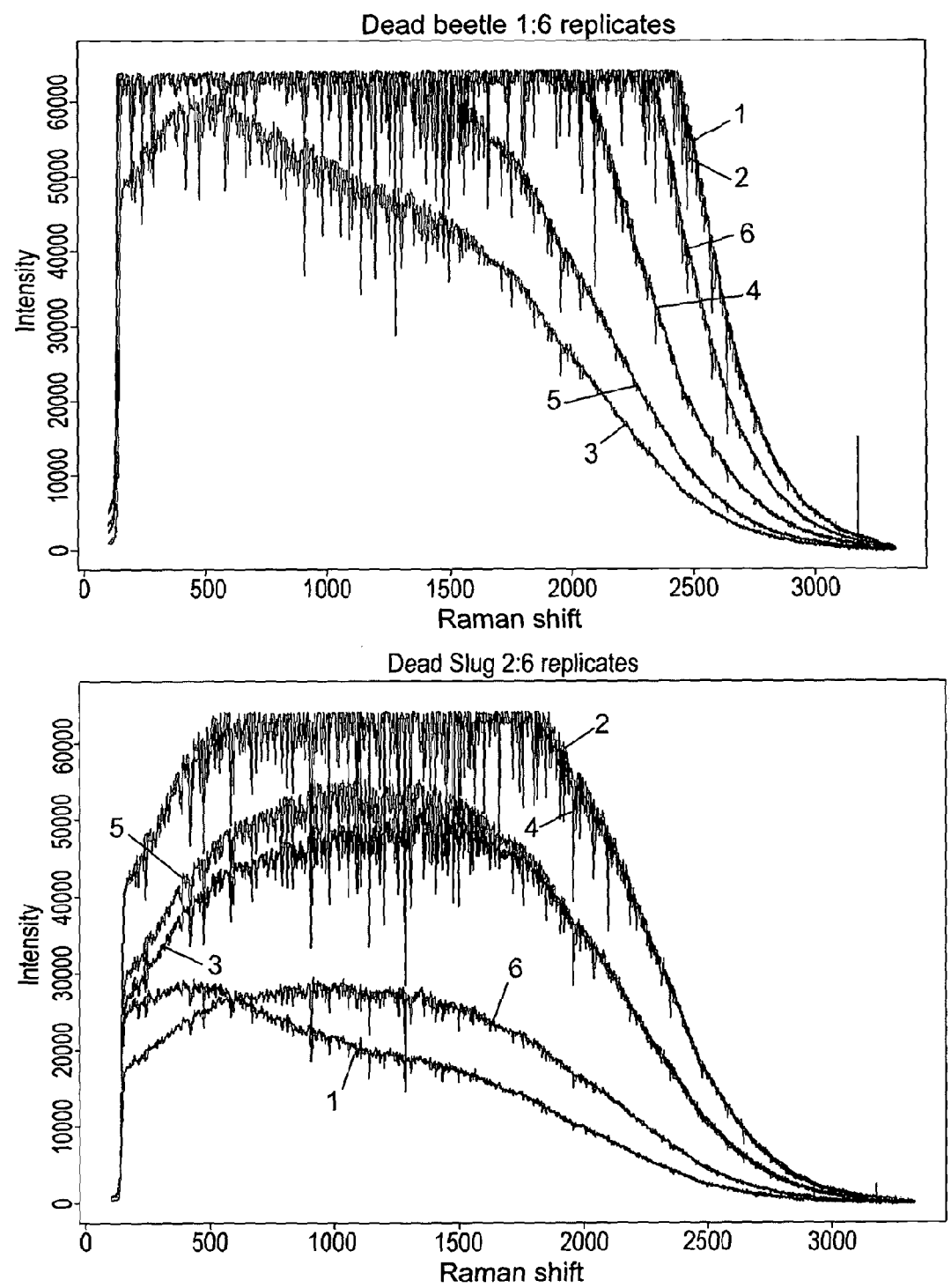
FIG. 11: Typical Raman spectra with 785 nm excitation showing broad fluorescence induced when invertebrate contamination is present.
Figure 11:
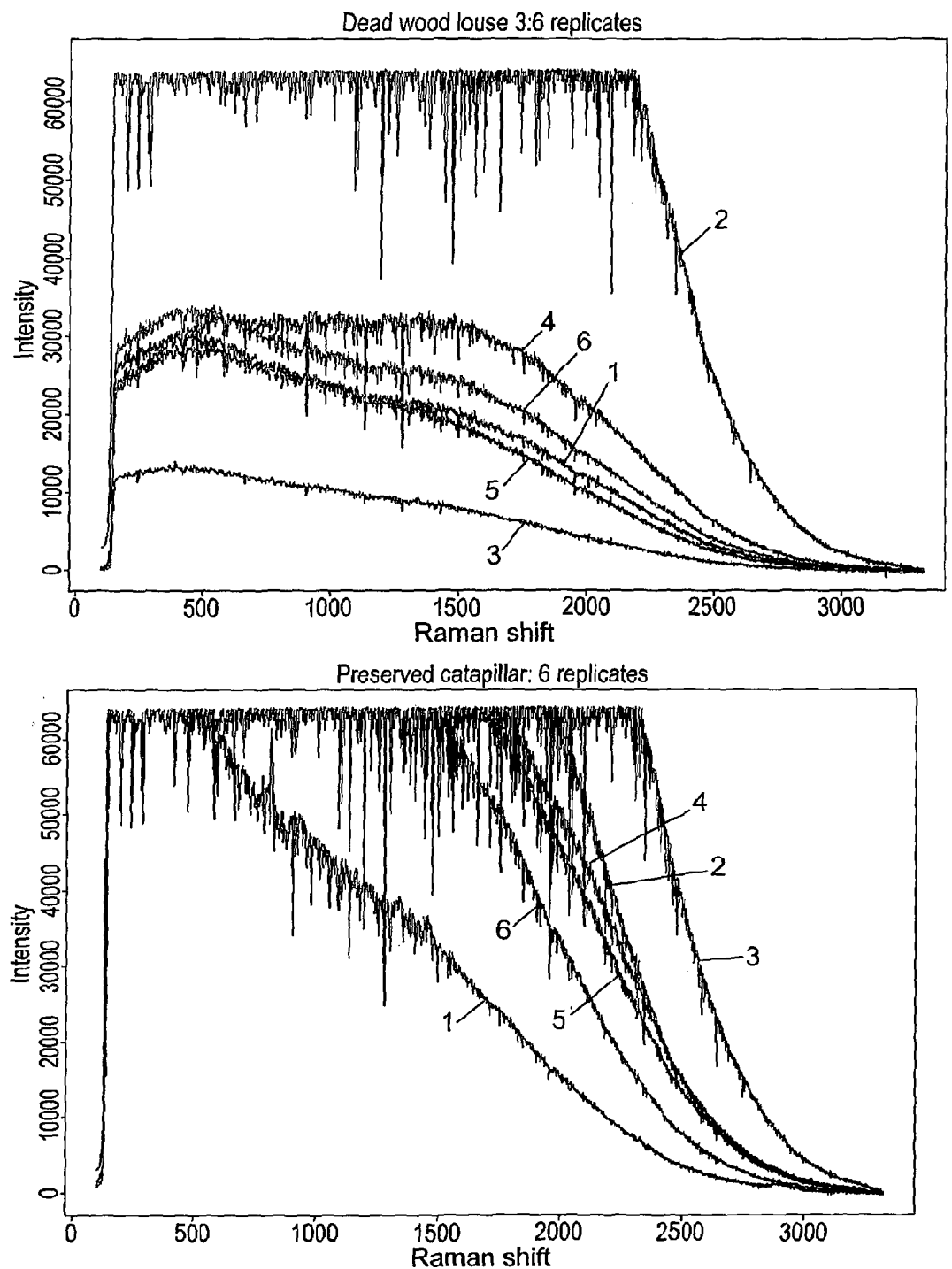
Figure 13:
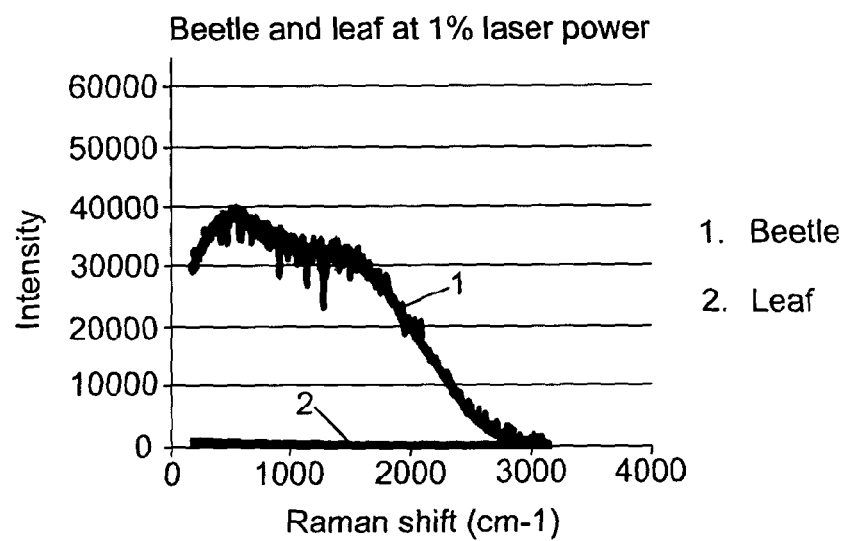
FIG. 13: Typical Raman spectra with (reduced) 785 nm excitation comparing directly, sample invertebrate with sample salad fluorescence response.

Spectra were collected on another independent Raman spectrometer with 785 nm excitation on a range of pest species, which confirmed the broad fluorescence effect (see FIGS. 11 and 13).

Figure 3:
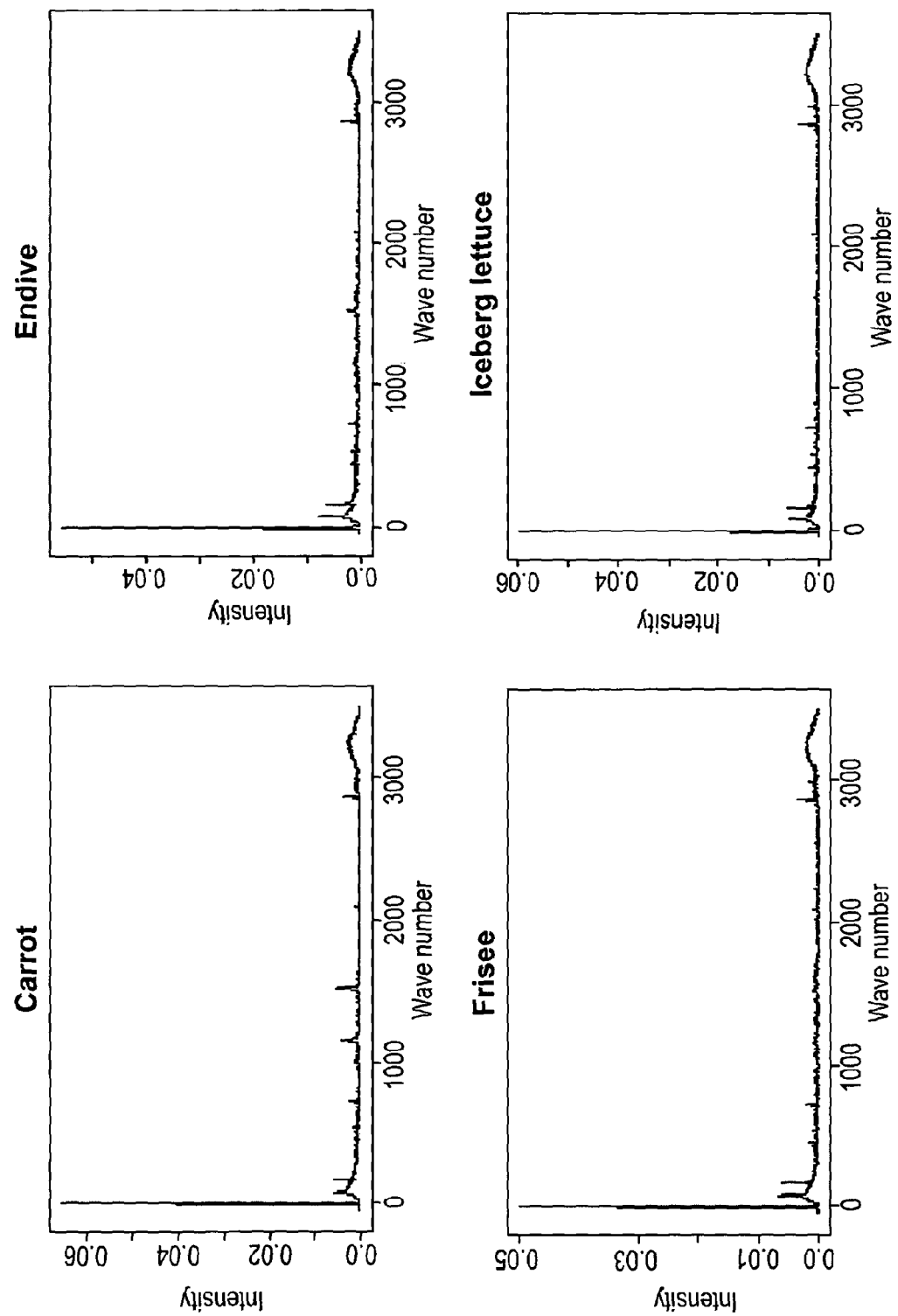
FIG. 3: Typical salad FT-Raman spectra with 1064 nm excitation with no sign of significant fluorescence when invertebrate contamination is not present.
Figure 12:
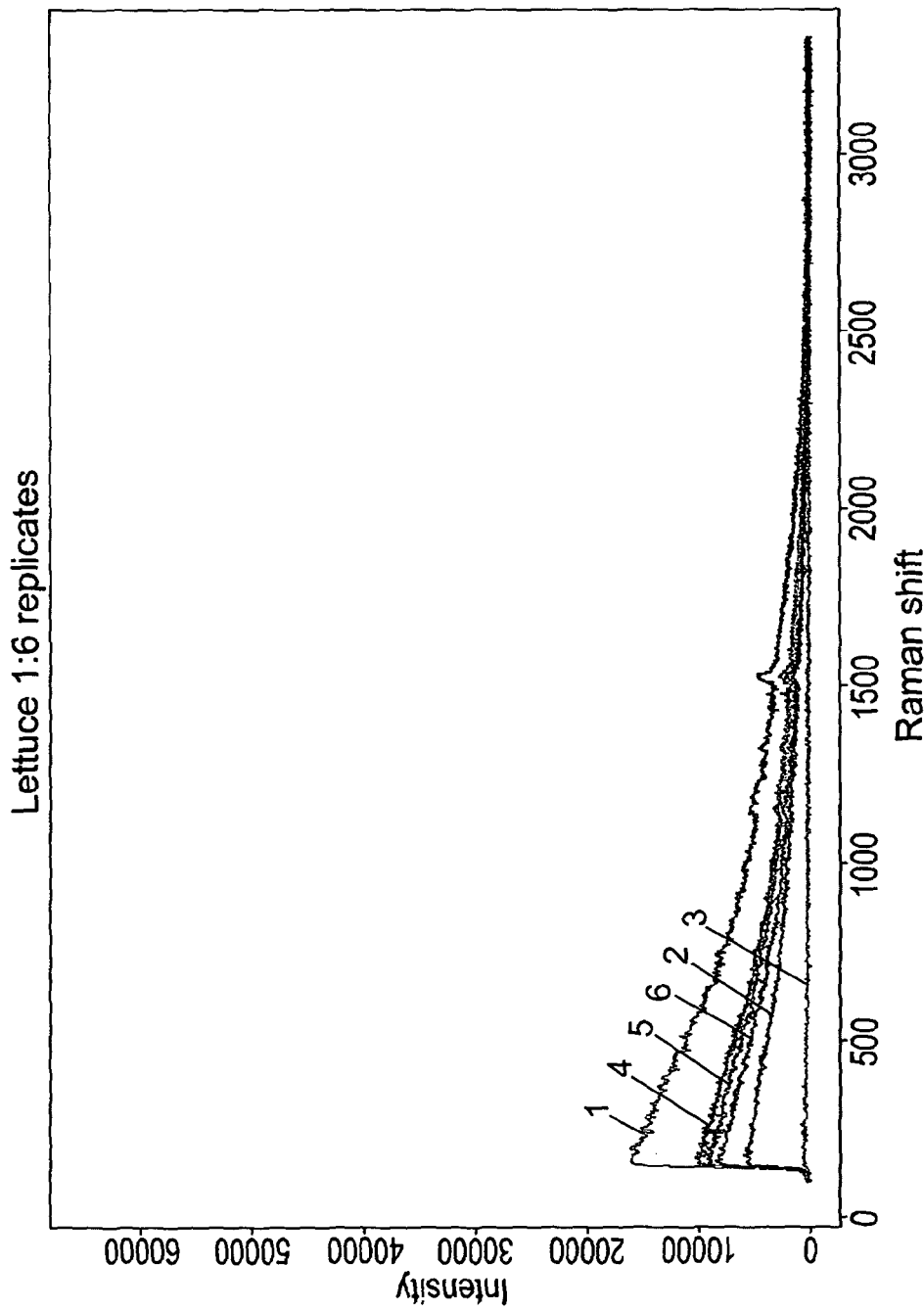
FIG. 12: Typical salad Raman spectra with 785 nm excitation with no sign of significant fluorescence when invertebrate contamination is not present.

Spectra were measured on thirteen types of salad crops: carrot, endive, frisee, iceberg lettuce, lamb's lettuce, lollo rosso, raddichio, radina lettuce, red chard, red oak lettuce, red pepper, rocket and spinach, see FIG. 3. All salad samples returned good spectra without fluorescence. FIGS. 3 and 12 show typical salad spectra with no sign of significant fluorescence. Thus, the selective fluorescence exhibited by the invertebrates appears to be a novel discovery.

Figure 8:
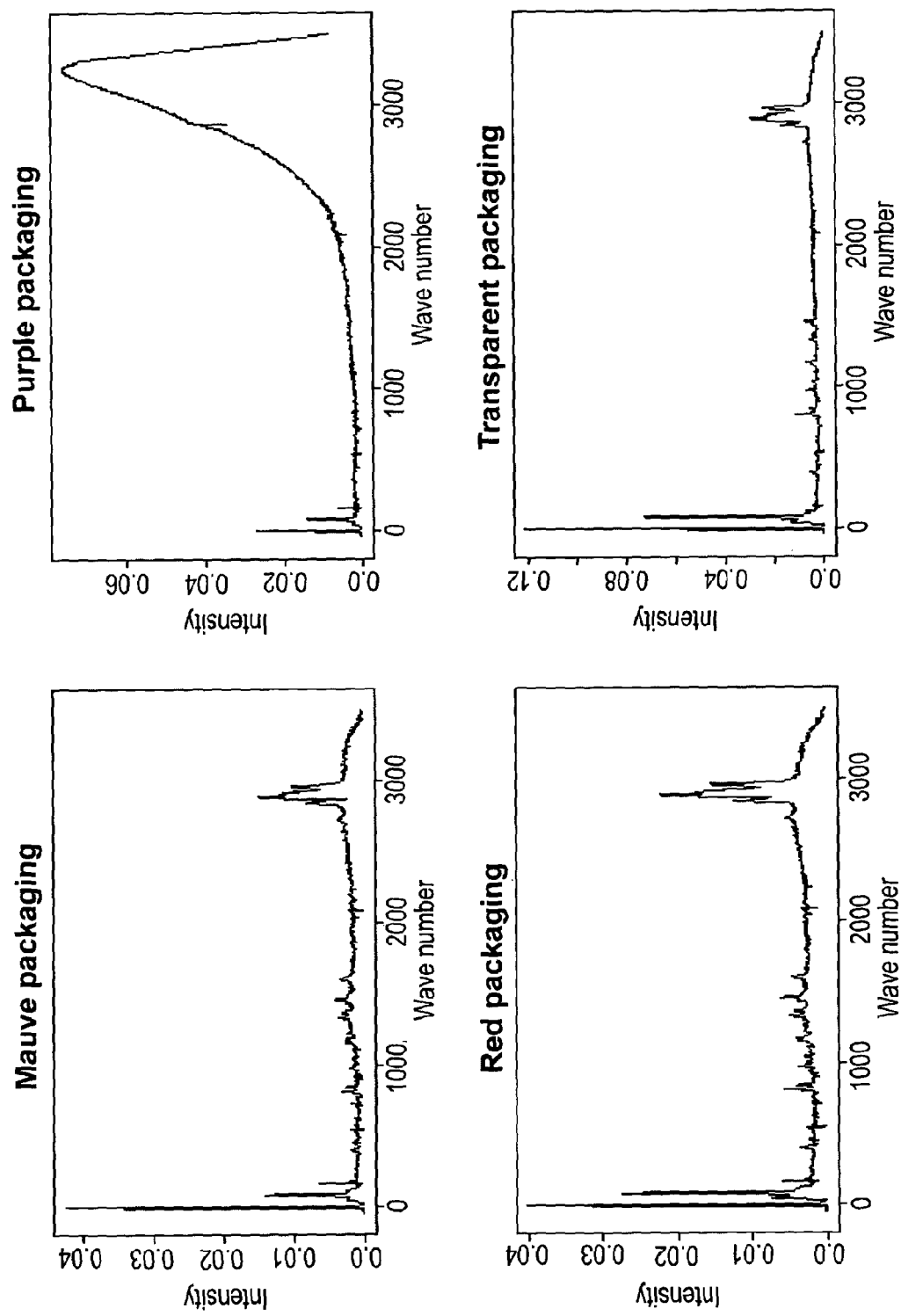
FIG. 8: FT-Raman spectra with 1064 nm excitation of different packaging materials, showing that most packaging materials are not thereby induced to fluoresce and that, therefore, those skilled in the art are easily able to select appropriate packaging material which does not negatively impact on the methodology disclosed herein.

Spectra were measured on five types of packaging mostly to assess the effect of the printing as a source of interference, see FIG. 8. One of the packaging samples showed a Raman spectrum with some fluorescence, but this was probably due to localised heating which would not occur under normal process measurement conditions. If this type of packaging continued to be an issue there is scope to eliminate it from use. Printed packaging samples were used since the ink was more likely to present a source of interferents. The high frequency feature seen within the 'purple packaging' spectrum appears to be due to heating effects.

Example 2

Effectiveness when the Contaminant is Obscured

The biggest difference between the spectra of the leaf and the beetle is the very high intensity of scattering right across the spectrum by the latter. This is valid for both sides of the beetle. This scattering is significant even when the beetle is hidden behind a leaf. Therefore instead of choosing a particular wavenumber for monitoring, integrated intensity across a broad wavenumber region should be the most sensitive discriminator.

Further, such strong scattering means a substantial reduction in light that is being transmitted. Therefore a combination of detection of both scattered and transmitted signals provides complementary information that would significantly improve the discrimination. Here it will be best to use a near IR laser frequency just outside the water overtone bands.

Figure 4:
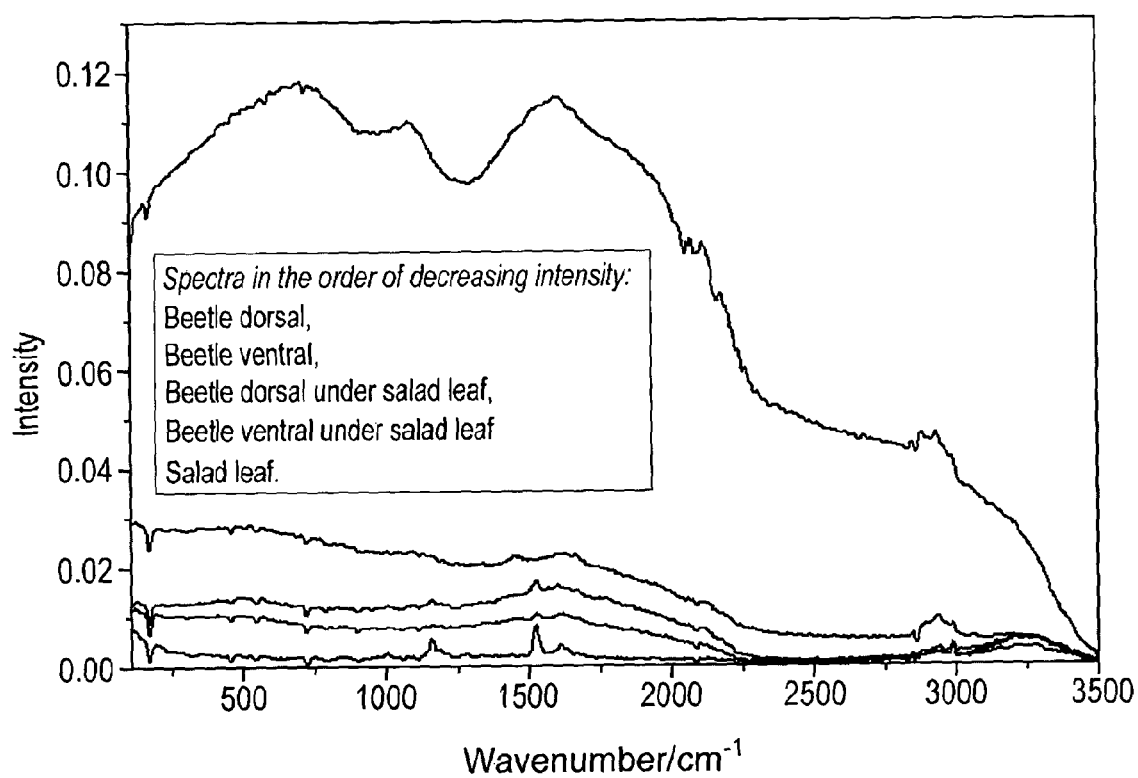
FIG. 4: FT-Raman spectra run with the 1064 nm excitation from a diode laser of insects compared to spectra when the insect is behind (i.e. obscured by) salad leaf material—showing that the insect is, detectable in either instance.

FIG. 4 shows FT-Raman spectra run with the 1064 nm excitation from a diode laser, showing the spectrum of a salad leaf; the spectrum of a beetle, the topside where the wings are; the spectrum of the beetle's topside through the salad leaf; the spectrum of a beetle, the bottom side where the legs are; the spectrum of the bottom side through the salad leaf.

Figure 14:
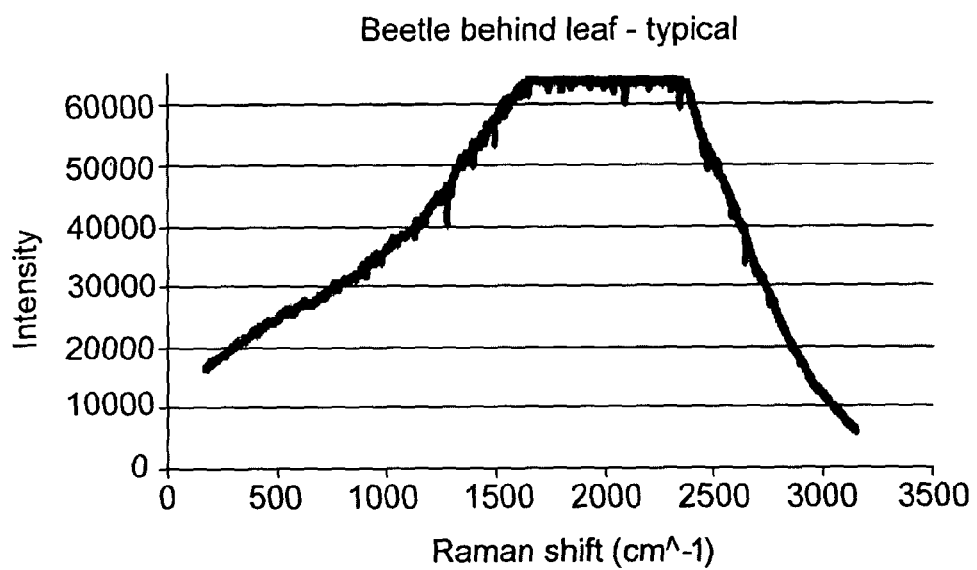
FIG. 14: Raman spectra run with the 785 nm excitation from a diode laser of sample invertebrate behind (i.e. obscured by) salad leaf material—showing that the invertebrate fluorescence response is still significantly different from uncontaminated salad leaf material, and detectable.

FIG. 14 shows Raman spectra run with the 785 nm excitation from a diode laser, topside of beetle through salad leaf.

Example 3

Source of the Fluorescence Effect

Figure 5:
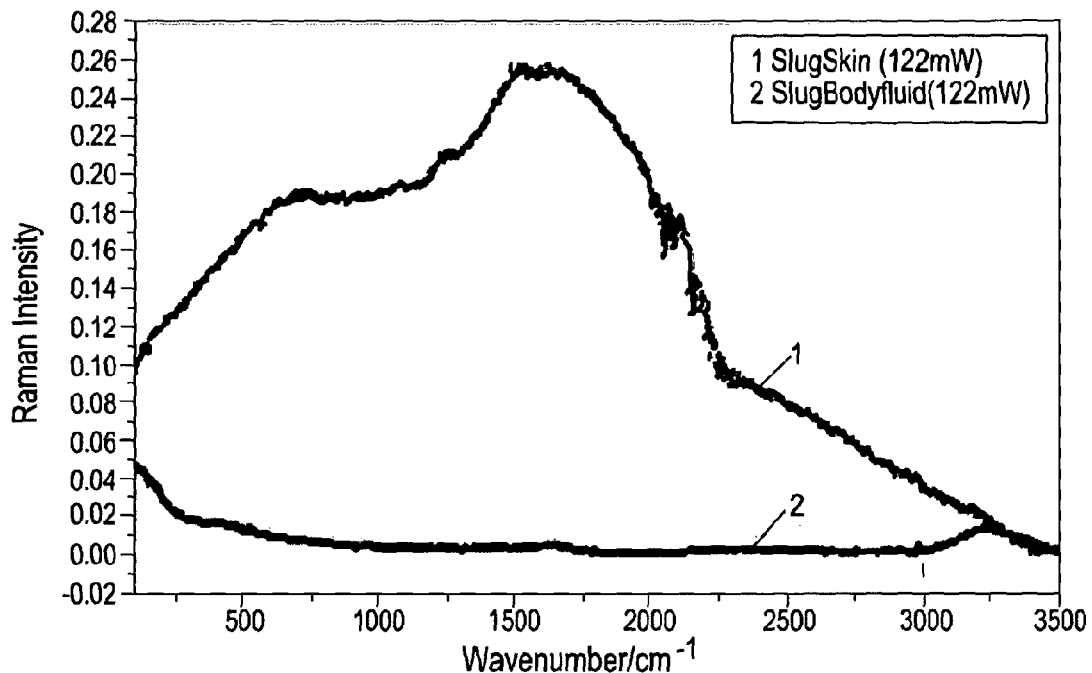
FIG. 5: FT-Raman spectra with 1064 nm excitation of slug skin as compared with slug body fluid.
Figure 6:
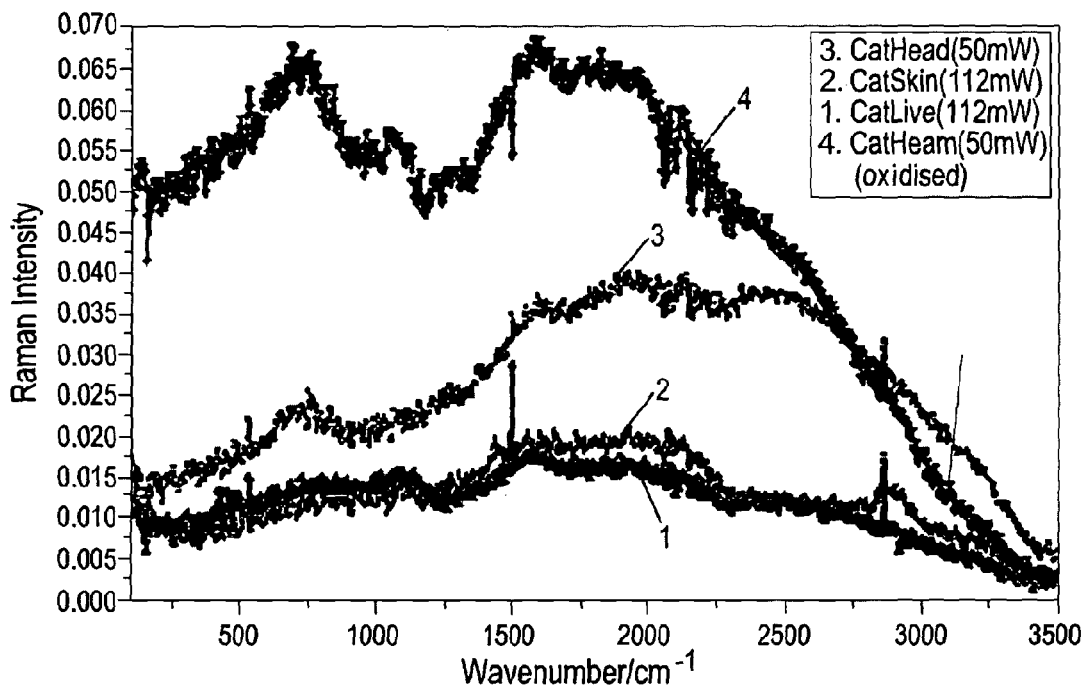
FIG. 6: FT-Raman spectra with 1064 nm excitation comparing fluorescence induced upon impingement on different body parts of a caterpillar.
Figure 7:
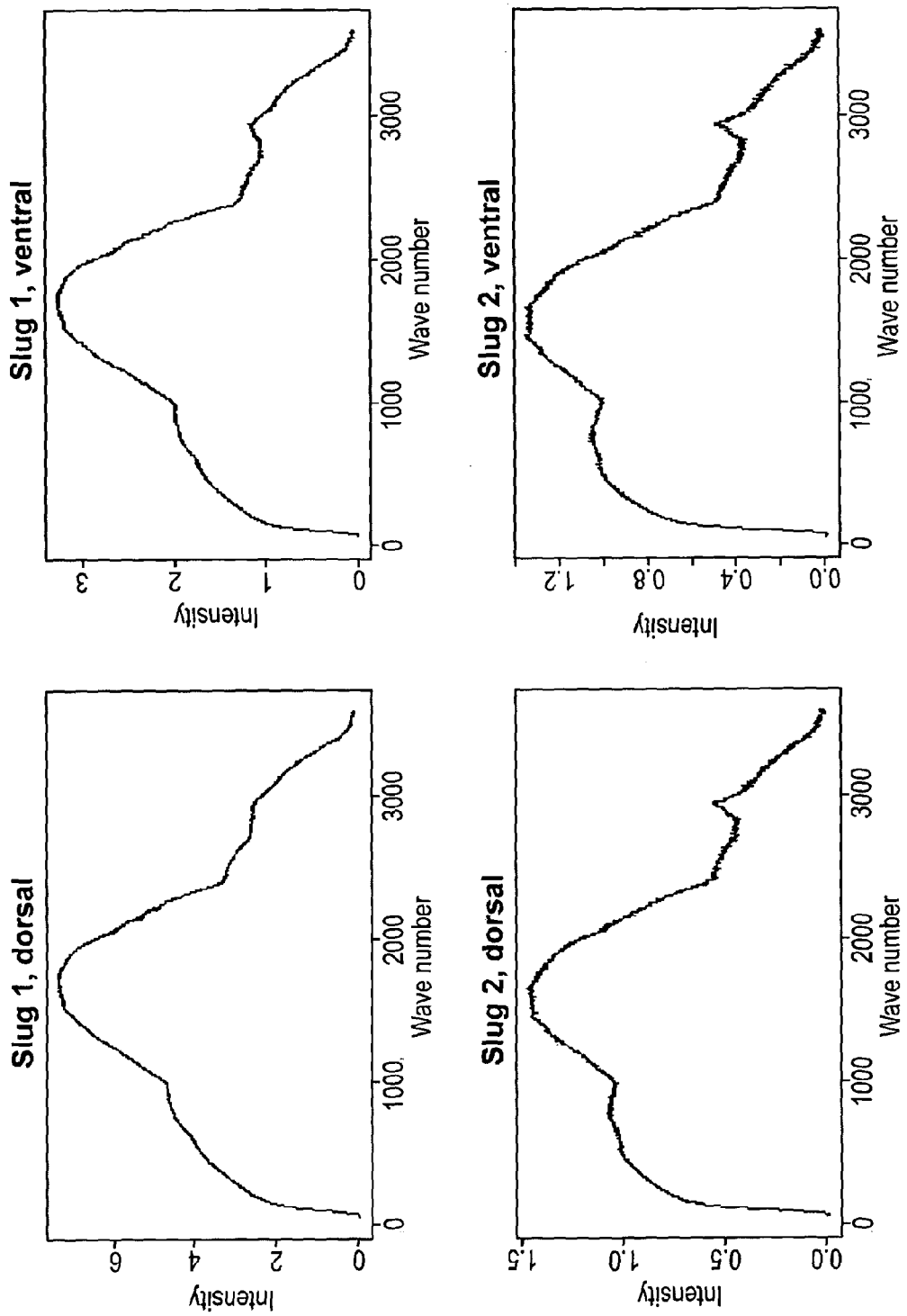
FIG. 7: FT-Raman spectra with 1064 nm excitation obtained from different views of a slug.

We have studied Slugs and Caterpillars in more detail and a brief summary of the results are given in FIGS. 5 and 6. We disclose fluorescence signals observed in the original spectra. However, the colourless body fluids from slugs do not show the fluorescence. Caterpillar hemolymph shows the strongest signals (see FIG. 6), while there are very slight differences in spectra between dead and live animals. These measurements are made with a laser beam focused to less than 0.5 mm diameter, so that there will be variations in the signal intensity due to sample presentation. This is the design of the FT-Raman spectrometer, which is designed to maximize the light throughput to the detector for maximum signal.

Figure 9:
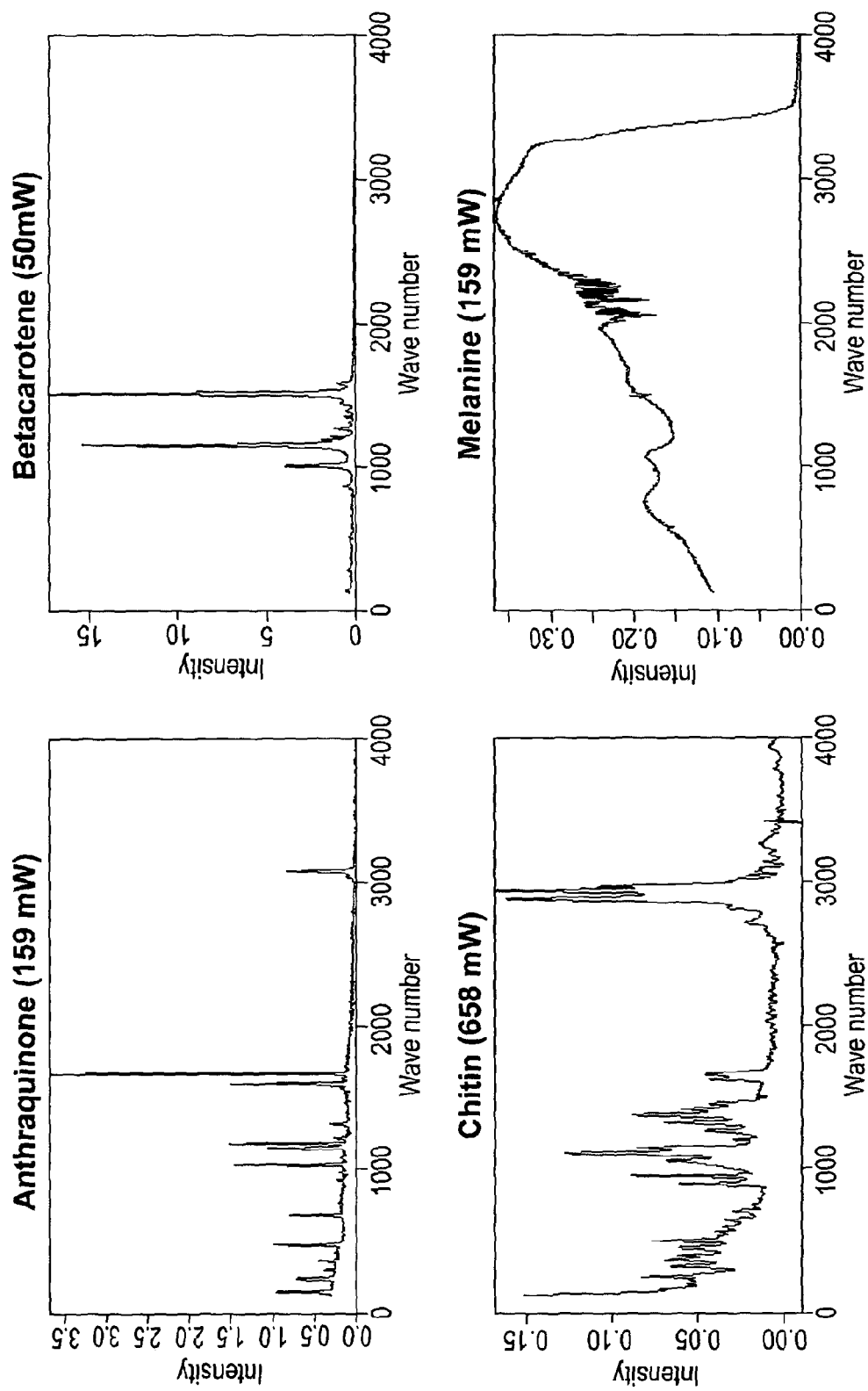
FIG. 9: FT-Raman spectra with 1064 nm excitation of some pigments (anthraquinone, betacarotene, chitin and melanin) that are candidates for the observed fluorescence effect reported herein on excitation at different wavelengths.

1064 nm excited FT-Raman spectra of anthraquinone, betacarotine, chitin and melanin are shown in FIG. 9. Of these, melanin is the only compound that shows broad fluorescence, while all the other pigments show sharp featured Raman spectra.

It is reasonable to expect the melanin fluorescence signals to be slightly modified depending on the environment of this molecule. Therefore the best candidate for a significant component of the fluorescence observed with these insects seem to be melanin. Our spectral observations for hemolymph is explicable in terms of the last stage of the biosynthetic process for melanin where 5,6-dihydroxyindole is oxidised by atmospheric oxygen to the polymeric material, melanin. This together with the fact that we have only observed fluorescence from the pigment melanin out of several potential candidates studied, strongly suggests that melanin is the pigment responsible for the fluorescence that we have observed from these insects. Of course, other contributing components may include haemolymph.

Example 4

Confirmation of the Nature of the Fluorophore

The haemolymph of the invertebrates is obtained by use of a fine hypodermic microsyringe inserted into the body cavity of the invertebrate. A cruder, less homogenous extract is also obtained by crushing the invertebrate so that a mixture of haemolymph and other body fluids is available for testing.

Raman spectroscopic measurements of these samples is used to test the hypothesis that the fluorophore detected by the method of this invention is haemolymph or a component thereof.

The Raman spectra from different body parts is obtained to see if there are differences between the wings, abdomen and legs, for example. This ensures that the presence of incomplete individuals is also detectable (i.e. that components of the contaminating pests are detectable). This also provides further insight into limitations of the sensitivity of the technique: the leaf density at which an insect is no longer detectable and whether the age of the insect affects its detection by this method.

FT-Raman spectroscopy is carried out with 1064 nm laser excitation. These measurements are accompanied by measurements of absorption spectra of each constituent, to establish the near-IR absorption features that are responsible for the observed fluorescence. A tuneable light source across the NIR (near infrared) to determine the fluorescence yields may be employed to determine the optimum excitation line to employ. Although another wavelength than 1064 nm may give a better sensitivity, there is also a trade-off against such factors as sample penetration depth and cost, since the more commonly used lasers are much cheaper to obtain.

Example 5

Detection of Insect Infestations in Meats

Figure 16:
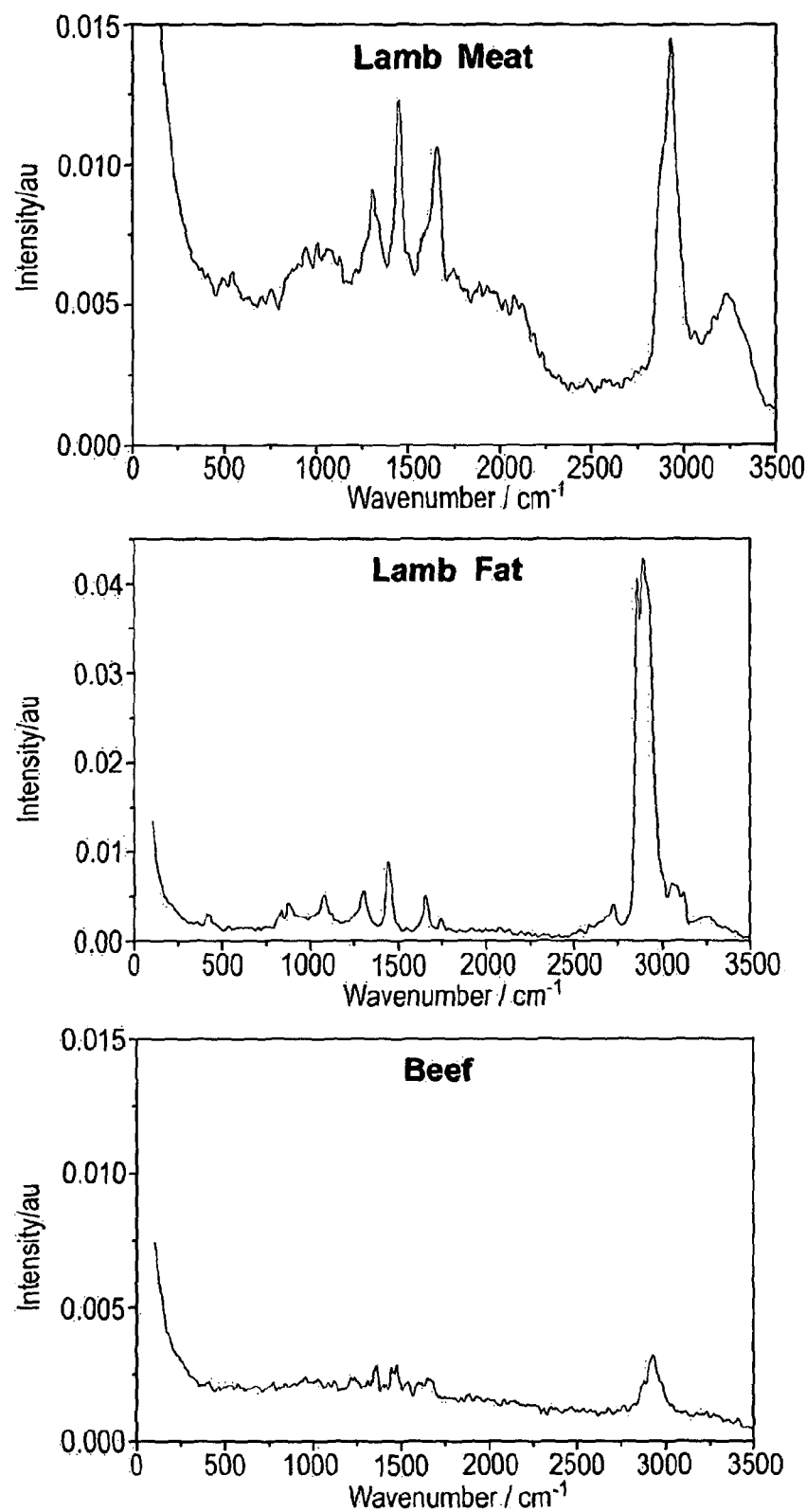
FIG. 16: Raman spectra of beef, pork, lamb and turkey (fresh, frozen and thawed samples) run using the 1064 nm laser excitation.
Figure 16:
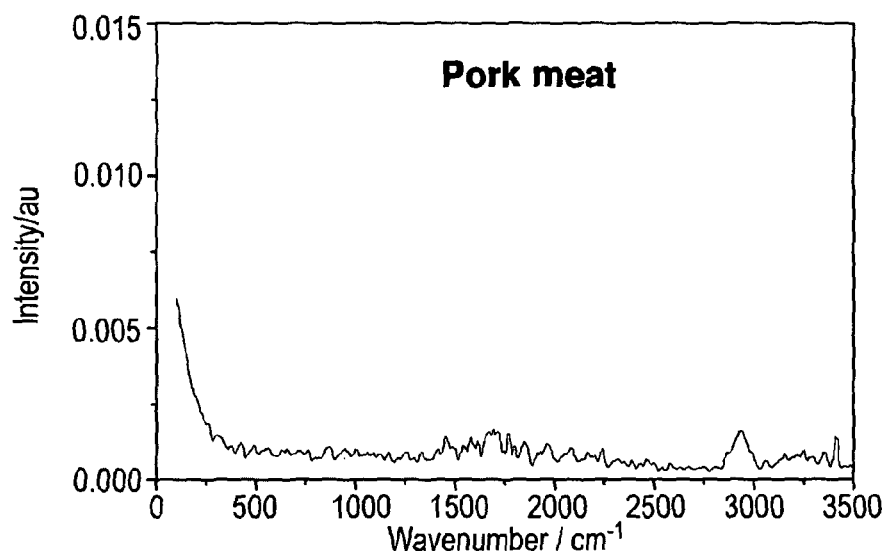
Figure 16:
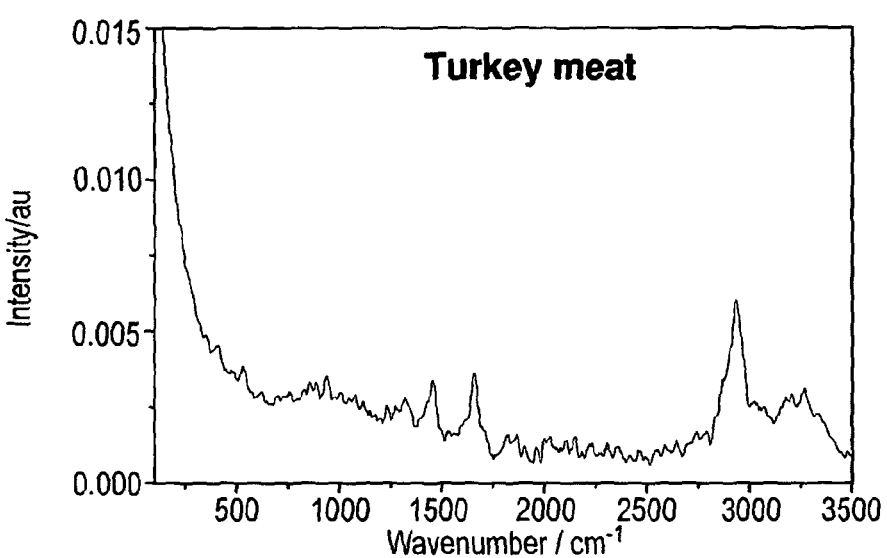

FIG. 16 shows Raman spectra of beef, pork, lamb and turkey (fresh, frozen and thawed samples) run using the 1064 nm laser excitation. None of these show any fluorescence effects as was expected, and the Raman spectra themselves are very weak in intensity (y-axis expanded for clarity) in spite of the use of a laser power of ~650 mW at the focus on the sample to a spot of ~150 microns diameter. The spectra are reminiscent of plant material, making them an excellent host for the detection method.

Example 6

Detection of Caterpillars in Plant Material

Figure 17:
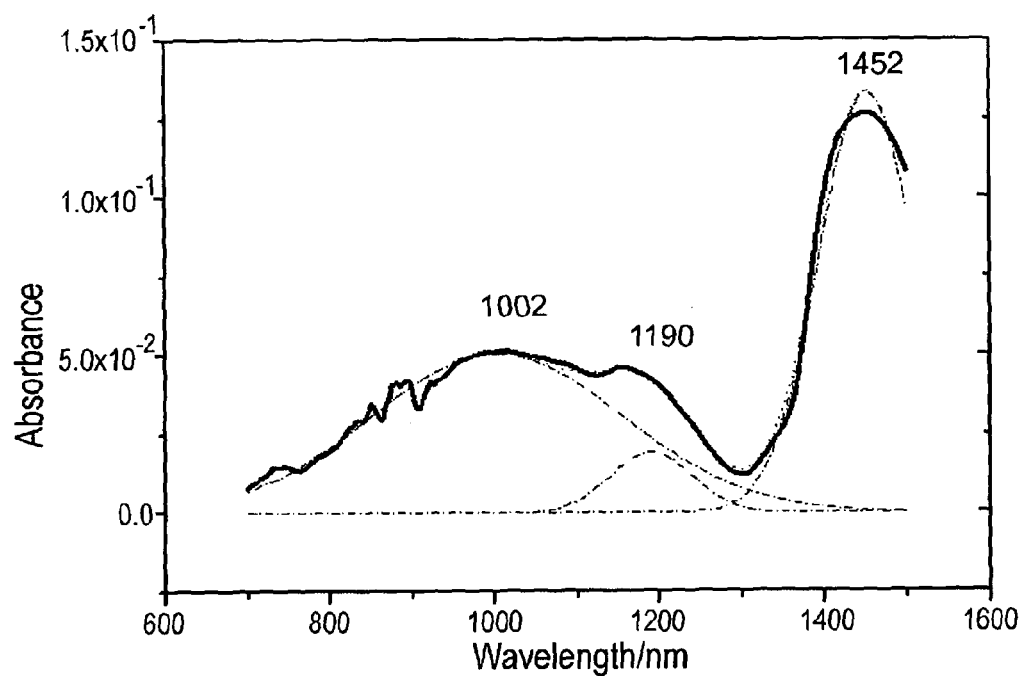
FIG. 17: The absorption spectrum of a live caterpillar.

Referring to FIG. 17, this shows an absorption spectrum of a live caterpillar, anaesthetised using $CO_2$ gas and held in place within a glass couvette. The measurement was done using a Hitachi U-4100 UV-Visible-NIR Spectrophotometer equipped with an integrating sphere sample attachment. The spectrum presented here is after a background subtraction accounting for the steady rise in the signal towards shorter wavelengths due to scattering. The spectrum was de-convoluted using the software package ORIGIN-PRO 8.5.1. The relatively sharp but weak features found around 900 nm are spurious features resulting from the automatic spectrometer adjustments needed for a continuous scan. The absorption at 1452 nm is assignable to the $1^{st}$ overtones of O—H and N—H bond vibrations and the 1190 nm band to the $2^{nd}$ overtones of $CH_3$, $CH_2$ and CH groups. It is not expected to see a strong broad absorption around 1002 nm arising from the vibrational overtones. Therefore this should be a very low lying electronic absorption, and is the origin of the Raman/fluorescence signal that we to use to provide the discrimination between plant and animal matter. There is a relatively intense absorption band spreading from ca 600 nm to 1400 nm. Therefore one would expect to see the fluorescence from excitations within this range of wavelengths, 600 to 1400 nm. However the most intense fluorescence is to be expected from excitation at the wavelength of ca 1002 nm or to the longer wavelengths of this, where one would expect the self-absorption of the fluorescent photons to be minimised. The spectrum was scanned using 700 to 1500 nm radiation.

Figure 18:
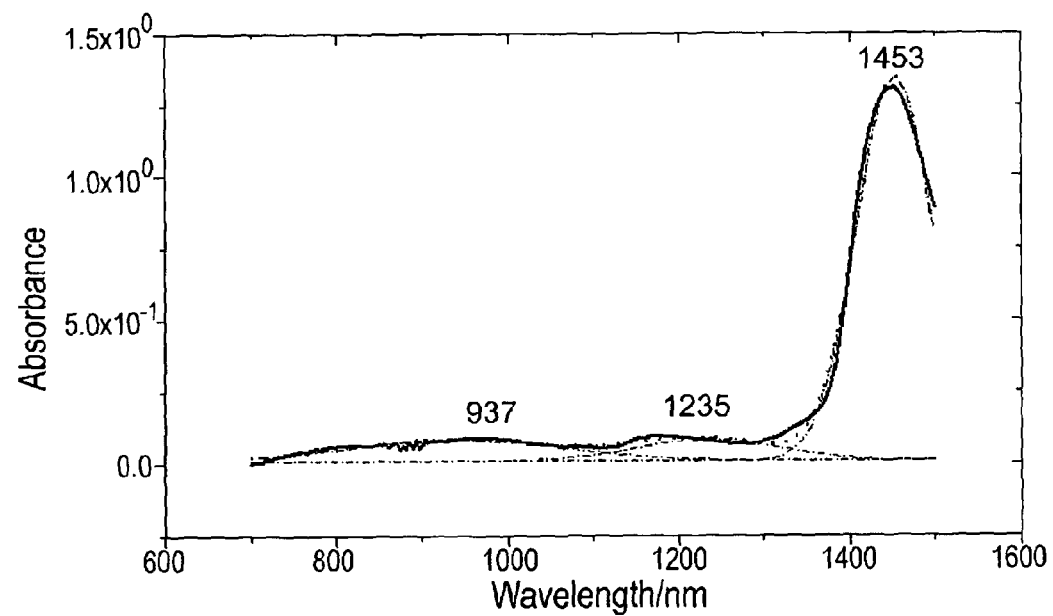
FIG. 18: The absorption spectrum of caterpillar hemolymph.

FIG. 18 shows the absorption spectrum of caterpillar hemolymph in a glass cuevette. This hemolymph sample was aged in air for a day when the colour changed from colourless to blackish brown. The measurement was done using a Hitachi U-4100 UV-Visible-NIR Spectrophotometer equipped with an integrating sphere sample attachment. The spectrum presented here is after a background subtraction accounting for the steady rise in the signal towards shorter wavelengths due to scattering. The spectrum was de-convoluted using the software package ORIGIN-PRO 8.5.1. The very weak features found around 900 nm are spurious features resulting from the automatic spectrometer adjustments needed for a continuous scan. The absorption at 1453 nm is assignable to the $1^{st}$ overtones of O—H and N—H bond vibrations and the 1235 nm band to the $2^{nd}$ overtones of $CH_3$, $CH_2$. The 937 nm band in the oxidised sample of hemolymph, which was absent in the fresh colourless sample of the hemolymph, covers a similar wavelength range to that at 1002 nm of the live caterpillar, and therefore assigned to the same electronic transition. The spectrum was scanned using 700 to 1500 nm radiation.

Example 7

Melanin Detection

We now describe evidence for the pigment Melanine (and/or a melanin precursor) being the material responsible for spectral discrimination we have observed, between the animal and plant species.

Figure 19A:
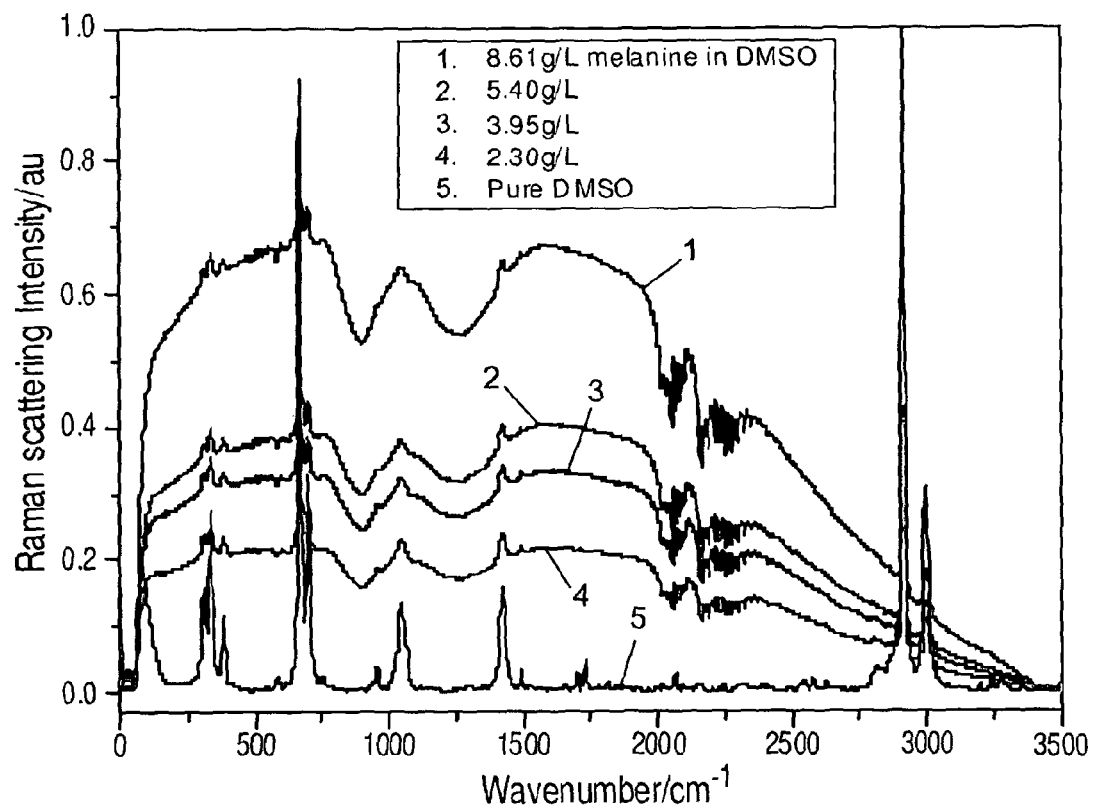
FIGS. 19a-c: Raman scattering of melanin against wavenumber; integrated scattering intensity against melanin concentration; and melanin absorbance spectrum, and with solvent and solvent contribution subtracted.

Solutions of four concentrations of synthetic melanine in the solvent dimethyl sulfoxide were made and the Raman spectra obtained using 1064 nm laser excitation. These spectra are shown in FIG. 19a. The observed scattering, when the sharp features due to the solvent has been removed, is clearly similar to those observed from the animal species found in the salad materials, described above. In FIG. 19a, although the y-axis is labelled Raman scattering, it could equally well represent fluorescence intensity. Similarly, chemical precursors to melanin also give rise to a fluorescence signal.

Figure 19B:
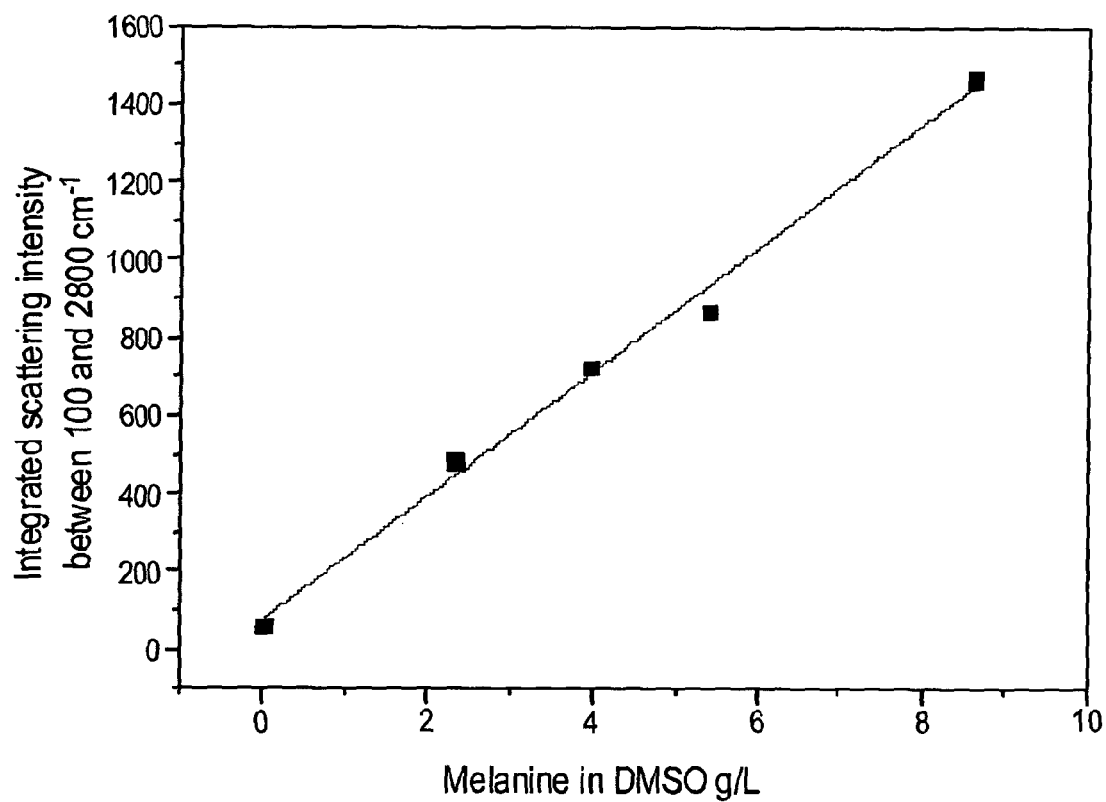

In order to check the quantitative dependence of these intensities on the concentration of melanine, the integrated intensity from 100 $cm^{-1}$ to 2800 $cm^{-1}$ for each of these samples were plotted against the concentration, in FIG. 19b, which shows the expected linear dependence.

Figure 19C:
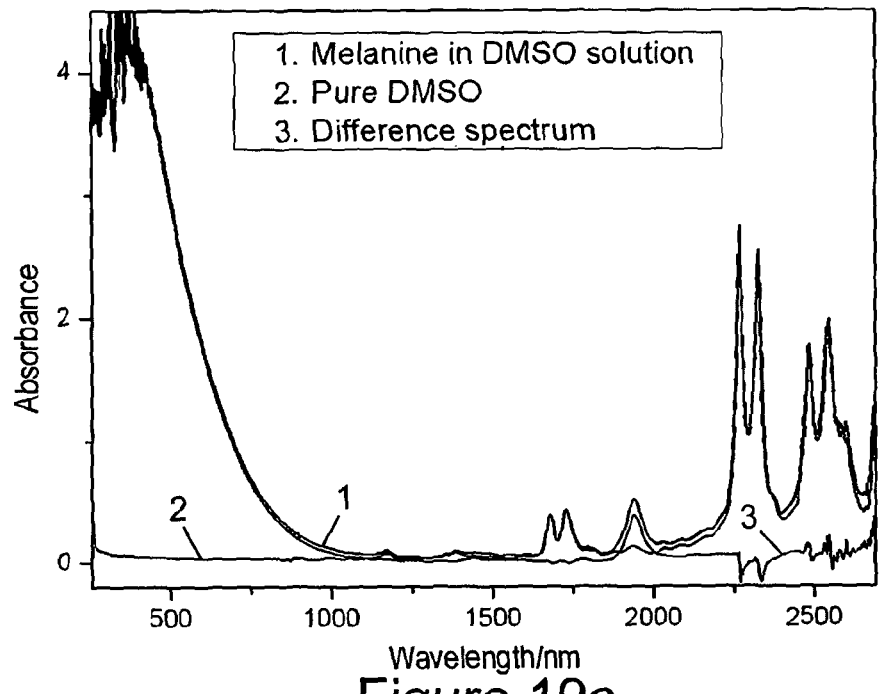

In order to detect the electronic absorption that is responsible for the observed fluorescence, absorption spectra covering the region 250 nm to 2750 nm, of the solution of melanine in DMSO, at a concentration of 8.61 g/L, (in black), and the pure solvent, (in red), were obtained, shown in FIG. 19c together with the melanine spectrum after the subtraction of the solvent spectrum, (in blue).

The pure melanine absorption spectrum, which is in blue, is dominated by an intense absorption peaking below ca 300 nm, and starting at around 1150 nm. There is also a weak peak at around 1900 nm. The long wavelength edge of the former band is responsible for the fluorescence observed in the Raman spectra with 1064 nm laser light. One can also predict from this spectrum that any excitations to the shorter wavelengths from this should show even more enhanced fluorescence. However in order to avoid re-absorption of the scattered radiation the observations are best conducted in the valley to the longer wavelengths from about 1000 nm. It is also important to avoid absorption bands due to overtones/combinations of water in the plant and animal matter, which appear at longer wavelengths than 1000 nm, for unhindered observation of the scattered radiation.

Figure 20:
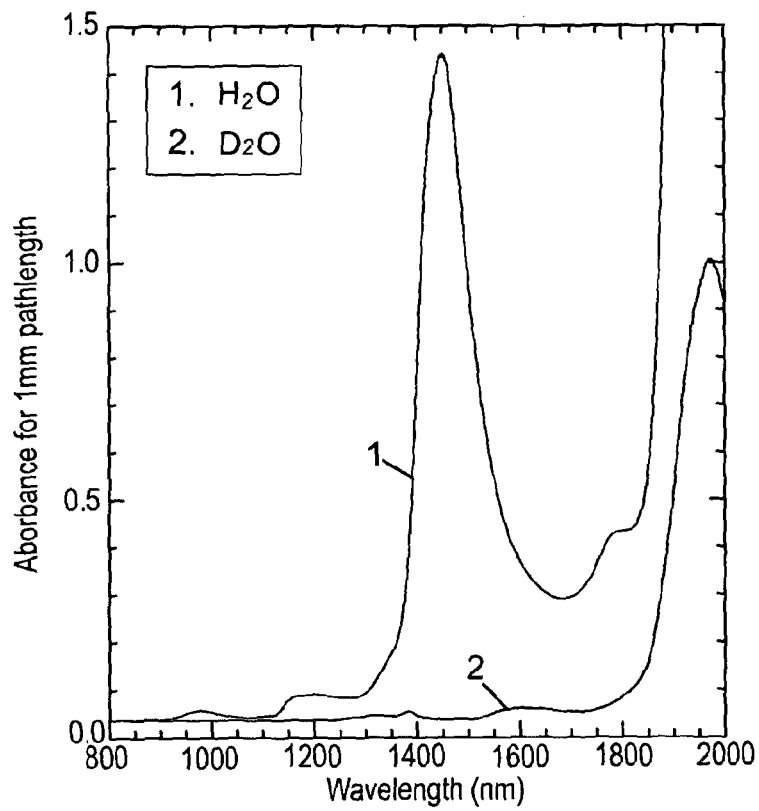
FIG. 20: Absorbance spectrum of water in the range 800-2000 nm.

As previously mentioned, some preferred embodiments of the techniques we employ use an excitation wavelength in a window which avoids absorption by both chlorophyll and water and which overlaps with the target fluorescence/Raman spectrum of melanin as indicated in FIG. 19. FIG. 10 shows absorbance by leaves, primarily chlorophyll, showing that for good transmittance through leaves it is advantageous to avoid the region just below 700 nm and the region below 550 nm; wavelengths above ~730 nm are preferred. FIG. 20 shows the absorbance spectrum of water in the region of interest, showing that there is an absorption peak at around 1450 nm (+/−50-100 nm) to avoid, as well as, preferably, wavelengths >1800 nm. Excitation with a tunable red/near IR laser in the range 750-110 nm has been found effective.

The above described techniques show significant potential for highly sensitive detection of the presence of a wide variety of invertebrate species and components thereof within a sample of plant or other material. Initial success has been obtained looking for the presence of several common species using pre-prepared foodstuffs, but the technique is generic and applicable to a variety of insect and pest detection applications including, for example, inspection of growing crops. The technique may also be applicable within bulk or process flow for a wide range of diverse products.

Some preferred implementations of the methods and apparatus we describe are for in-line detection of insect contamination of foodstuff and other product processing streams. Optionally embodiments of the method/system may be incorporated into a foodstuff quality control line employing a conveyor belt or other product feed system and one or both of a user alert and a system to automatically remove contaminated foodstuff from the line.

Figure 21:
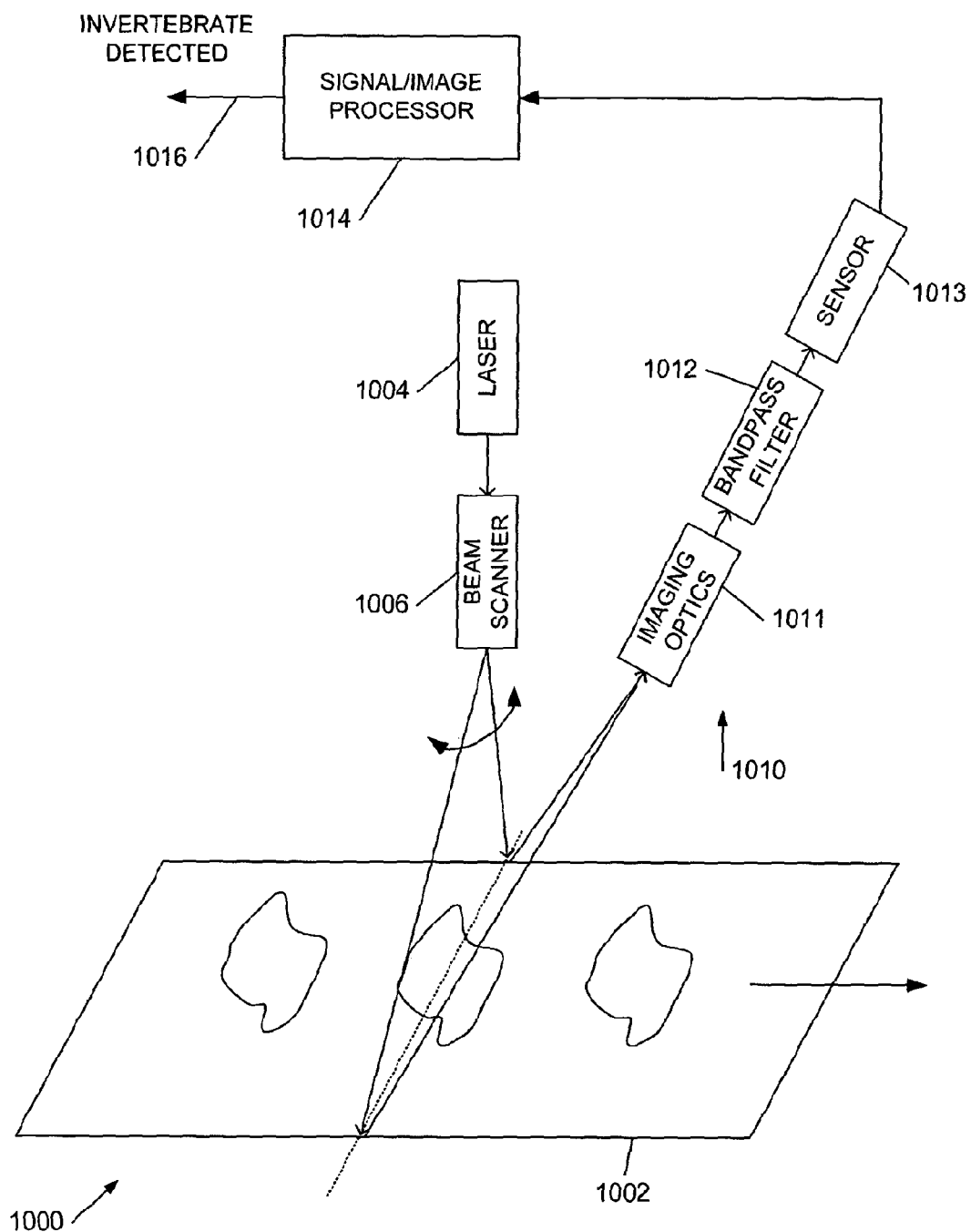
FIG. 21: Example apparatus for implementing embodiments of the invention.

Thus FIG. 21 shows an example implementation of a foodstuff inspection system 1000 configured to implement embodiments of the above described techniques. The example system comprises a conveyor belt 1002 across which an IR laser 1004 in combination with an optical beam scanner 1006 defines a scanned illumination line. A camera system 1010 to detect the fluorescence response comprises imaging optics 1011 to image a signal from a scanned foodstuff 1008 onto a sensor 1013 via one or more bandpass interference filters 1012, to select the wavelength(s) of interest, as described previously. The camera system 1010 provides an input to signal/image processing system 1014 which applies time and/or spatial integration and thresholding to provide an output 1016 to identify when undesired invertebrate matter is likely to be present.

Embodiments techniques we have described may in principle be used with a wide range of Raman and/or fluorescence spectroscopy systems. For example, embodiments of the above described methods and systems may detect light from one or both of Stokes Raman scattering and anti-Stokes Raman scattering and/or fluorescence, in particular under near IR (laser) irradiation. The scattered light may be interrogated at a single point on the foodstuff or over a region (and optionally integrated), or the Raman response may be imaged, or hyperspectral imaging of the scattered light may be performed.

No doubt many other effective alternatives will occur to the skilled person. It will be understood that the invention is not limited to the described embodiments and encompasses modifications apparent to those skilled in the art lying within the scope of the claims appended hereto.

The invention claimed is:

1. A method for detection of the presence of an invertebrate or an invertebrate component, wherein said invertebrate or invertebrate component comprises melanin or one or more chemical precursors to melanin, in a sample of substantially non-invertebrate material, comprising:
impinging said sample with a source of electromagnetic radiation at a wavelength of at least 600 nm; and
detecting fluorescence of said invertebrate or said component of said invertebrate based on a presence of said melanin or one or more chemical precursors to melanin at a wavenumber where the non-invertebrate components of said sample either do not fluoresce or fluoresce with an intensity below a threshold;
wherein the non-invertebrate material is edible and/or living.

2. The method according to claim 1 wherein the sample is plant material.

3. The method according to claim 1 which comprises making a comparison between Raman and fluorescence spectra.

4. The method according to claim 3 wherein said Raman spectra comprise signals from non-invertebrate components in said sample and signals from said invertebrate or said invertebrate component in said sample, whereas said fluorescence signal is provided only by said invertebrate or invertebrate component in said sample, wherein said latter signal is greater than the former.

5. The method according to claim 1 wherein said excitation wavelength is selected from a wavelength of about 750 nm to about 1064 nm.

6. A method as claimed in claim 1 wherein said wavelength is in the range 750 nm to 1100 nm to reduce absorption of said fluorescence response by both chlorophyll and water;

wherein said fluorescence is detected at greater than 50 nm from said wavelength, the method comprising detecting melanin by distinguishing a broadband response from a sharper peaked response, wherein the method is used for detecting invertebrate contamination within packaging when said invertebrate contamination is at least partially obscured by said foodstuff.

7. The method according to claim 1 wherein said invertebrate is an invertebrate comprising haemolymph, and wherein said detecting of said fluorescence detects said haemolymph.

8. The method according to claim 7 wherein said invertebrate is selected from the group consisting of beetles, caterpillars, moths, slugs and spiders.

9. The method according to claim 1 wherein said method is utilized in the detection of contamination of prepared foods, raw materials, infestation of crops including scanning of growing plants in glasshouses and in fields, biosecurity threats including scanning of plant material during import and export, examination of plants and cut flowers for infestation in horticultural applications, or detection of insect infestations including termites and deathwatch beetle.

10. The method according to claim 9 for use in reducing or targeting the use of pesticides.

11. A method as recited in claim 1 for detecting the presence of an invertebrate or an invertebrate component in a plant-based foodstuff when said invertebrate/component is obscured by said foodstuff, the method comprising using fluorescence/Raman spectroscopy to detect said melanin and/or a said melanin precursor in said foodstuff, wherein said fluorescence/Raman spectroscopy employs optical excitation at a wavelength longer than 600 nm, and detects fluorescence/Raman scattering from said invertebrate or invertebrate component.

12. An optical foodstuff quality control system for detecting the presence of an invertebrate or an invertebrate component, wherein said invertebrate or invertebrate component comprises melanin and/or one or more chemical precursors to melanin, in a plant-based foodstuff, the system comprising:

a fluorescence/Raman spectrometer configured to remotely interrogate a fluorescence/Raman scattering response of said foodstuff; and a data analysis system, coupled to said fluorescence/Raman spectrometer, configured to analyze said fluorescence/Raman scattering response to determine the presence of said invertebrate/invertebrate component dependent on a level of said melanin and/or a said melanin precursor indicated by said fluorescence/Raman scattering response.

13. A system as claimed in claim 12 wherein said fluorescence/Raman spectrometer comprises:

a sample illumination system configured to illuminate said foodstuff, said sample illumination system comprising an optical excitation source having a wavelength of greater than 600 nm;

a light collection system configured to collect fluorescence/Raman scattered light from said foodstuff;

wavelength selection optics, coupled to said light collection system, configured to attenuate light at a wavelength of said optical excitation source; and a detector, in an optical path following said wavelength selection optics, configured to detect said fluorescence/Raman scattered light.

14. A system as claimed in claim 13 wherein said data analysis system is configured to distinguish a broadband fluorescence/Raman scattering response from sharper peaked fluorescence/Raman scattering responses to identify presence of said melanin.

15. A system for detection of the presence of an invertebrate or an invertebrate component, wherein said invertebrate or invertebrate component comprises melanin or one or more chemical precursors to melanin, in a sample of substantially non-invertebrate material, the system comprising:

(a) a source of electromagnetic radiation configured to impinge said sample with electromagnetic radiation at a wavelength of at least 600 nm or 700 nm; and (b) a fluorescence detector configured to detect fluorescence of said invertebrate or invertebrate component based on a presence of said melanin or one or more chemical precursors to melanin at a wavenumber where the non-invertebrate components of said sample either do not fluoresce or fluoresce with an intensity below a threshold.

16. The system according to claim 15 wherein both Raman and fluorescence spectra are obtained.

17. An apparatus for detection of the presence of an invertebrate or an invertebrate component, wherein said invertebrate or invertebrate component comprises melanin or one or more chemical precursors to melanin, in a sample of substantially non-invertebrate material, said apparatus comprising:

(a) a source of electromagnetic radiation configured to impinge said sample with electromagnetic radiation at a wavelength of at least 600 nm; and (b) a fluorescence detector configured to detect fluorescence of said invertebrate or an invertebrate component based on a presence of said melanin or one or more chemical precursors to melanin at a wavenumber where the non-invertebrate components of said sample do not fluoresce or fluoresce with an intensity below a threshold.

18. The apparatus according to claim 17 further comprising:

(a) an optical train for delivering said electromagnetic radiation onto said sample;

(b) collection optics;

(c) at least one detector or detection system; and (d) a decision engine configured to process the signals produced by the detector and to discriminate an invertebrate contamination detection signal from noise.

19. The apparatus according to claim 18 wherein, depending on the nature of signals obtained from the sample, said decision engine provides an indication that invertebrate contamination is detected in the sample.

20. The apparatus according to claim 19 wherein, when contamination is detected, a rejection mechanism results in the segregation of contaminated material from non-contaminated material.

* * * * *